United States Patent [19]
Wiederin

[11] Patent Number: 5,272,308
[45] Date of Patent: Dec. 21, 1993

[54] DIRECT INJECTION MICRO NEBULIZER AND ENCLOSED FILTER SOLVENT REMOVAL SAMPLE INTRODUCTION SYSTEM, AND METHOD OF USE

[75] Inventor: Daniel R. Wiederin, Omaha, Nebr.

[73] Assignee: Cetac Technologies Inc., Omaha, Nebr.

[21] Appl. No.: 980,467

[22] Filed: Nov. 23, 1992

Related U.S. Application Data

[63] Continuation-in-part of Ser. No. 813,766, Dec. 27, 1991, Pat. No. 5,212,365.

[51] Int. Cl.$^5$ ............................................. B23K 9/00
[52] U.S. Cl. ........................... 219/121.52; 219/121.59; 219/121.51; 315/111.51; 239/338
[58] Field of Search ............... 219/121.43, 121.52, 219/121.51, 121.59; 315/111.21, 11.51; 239/338; 250/288

[56] References Cited

U.S. PATENT DOCUMENTS

| | | | |
|---|---|---|---|
| 4,766,287 | 8/1988 | Morrisroe et al. | 219/121.52 |
| 4,926,021 | 5/1990 | Streusand et al. | 219/121.59 |
| 5,051,557 | 9/1991 | Satzger | 219/121.52 |
| 5,187,344 | 2/1993 | Mizuno et al. | 219/121.5 |

*Primary Examiner*—Mark H. Paschall
*Attorney, Agent, or Firm*—James D. Welch

[57] ABSTRACT

A direct injection micro nebulizer based sample introduction system for use in nebulizing sample solutions in close proximity to sample analysis systems, with desolvation and solvent removal capability is disclosed. The present invention offers design features and utility not available in previously known micro nebulizer systems. Predominantly unibody design and use of nonmetalic, hydrofloric acid resistant construction materials are taught. The present invention allows easy cleaning and adjustment of element relationships which are necessary to proper operation of direct injection micro nebulizer systems. Use of separate or integrated protective sleeving on otherwise crushable sample solution delivery tubing is disclosed. Special direct injection micro nebulizer top elements and torch designs are also disclosed.

45 Claims, 4 Drawing Sheets

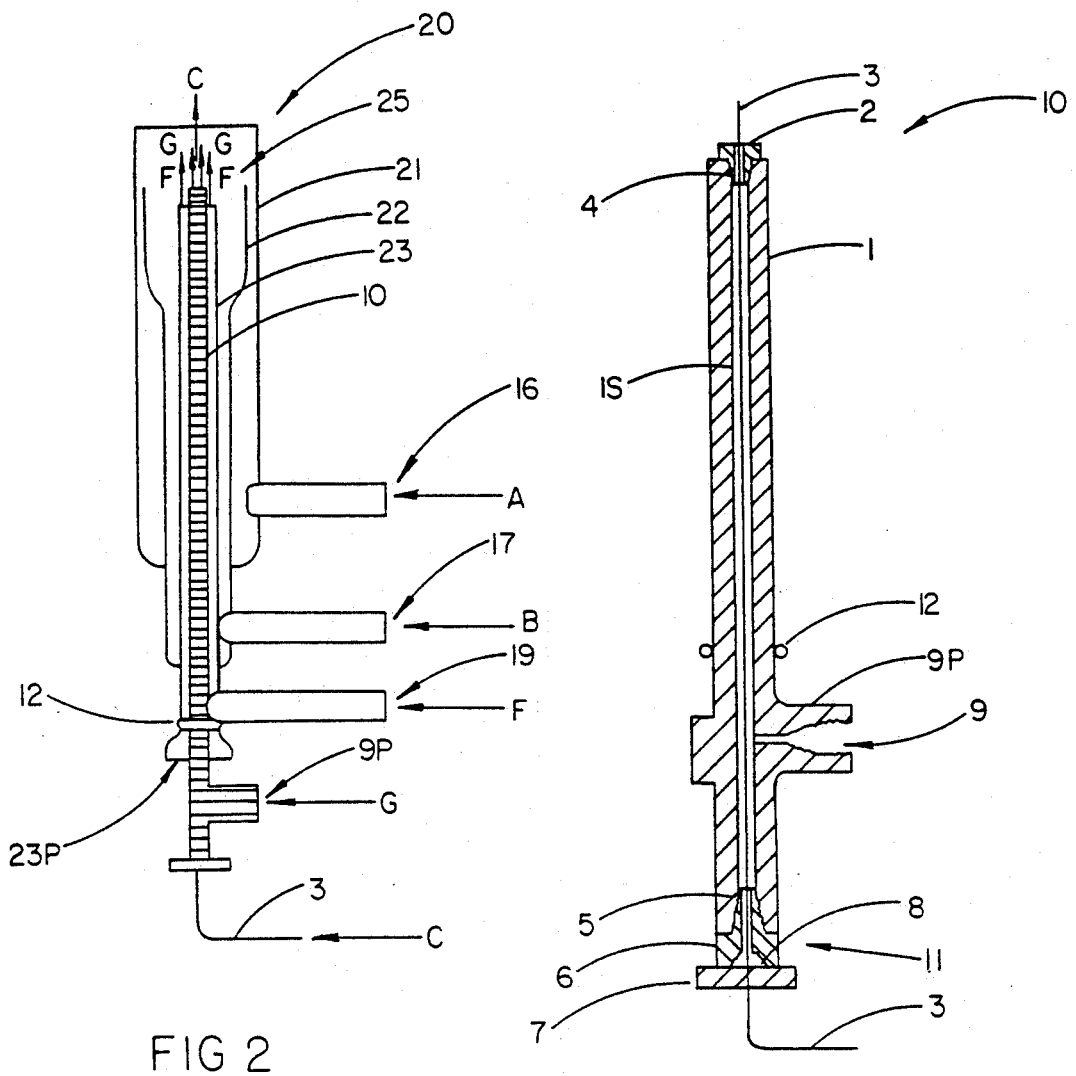
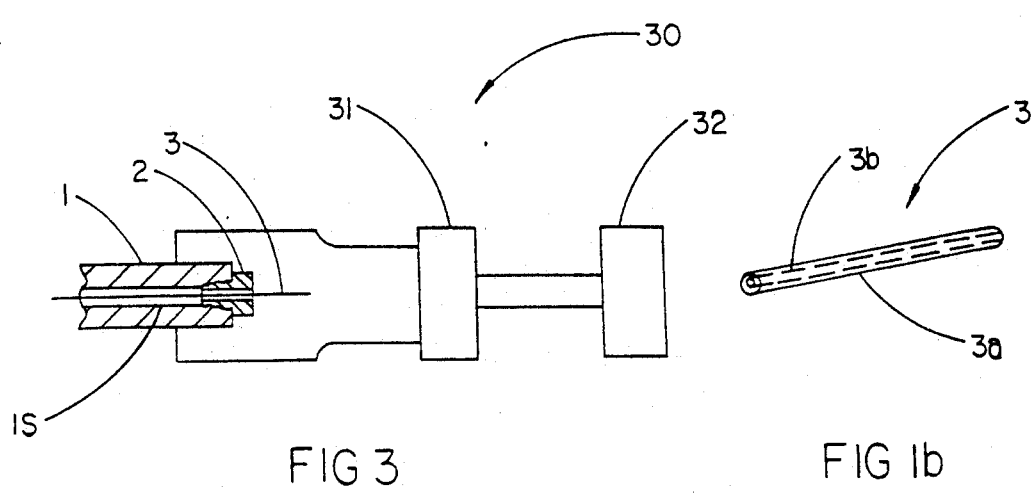

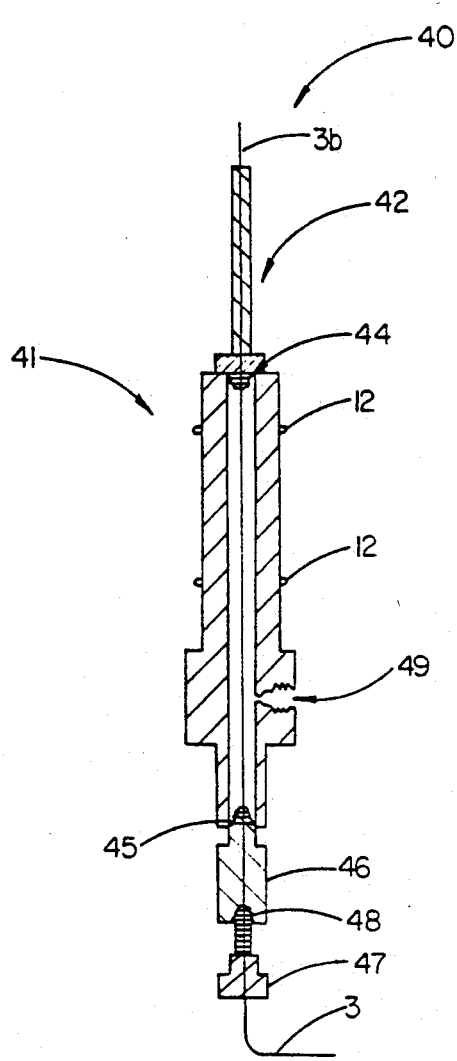
FIG. 4
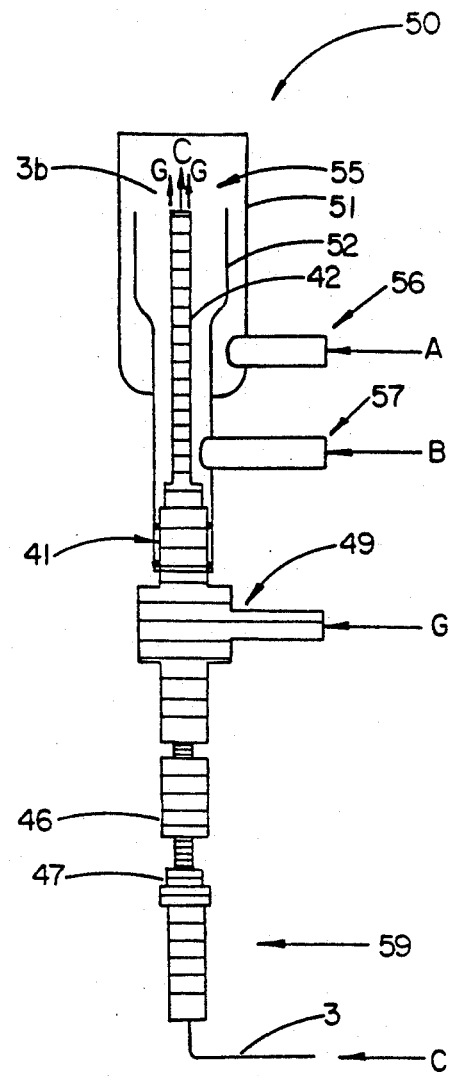
FIG. 5
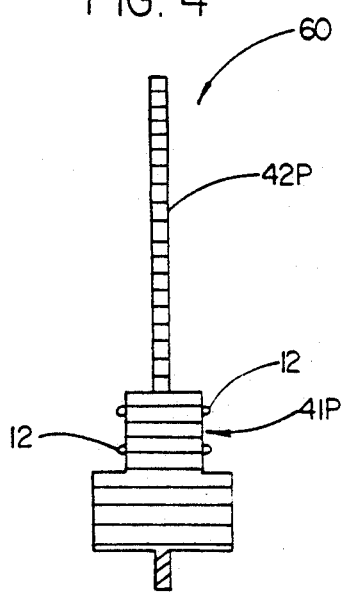
FIG. 6
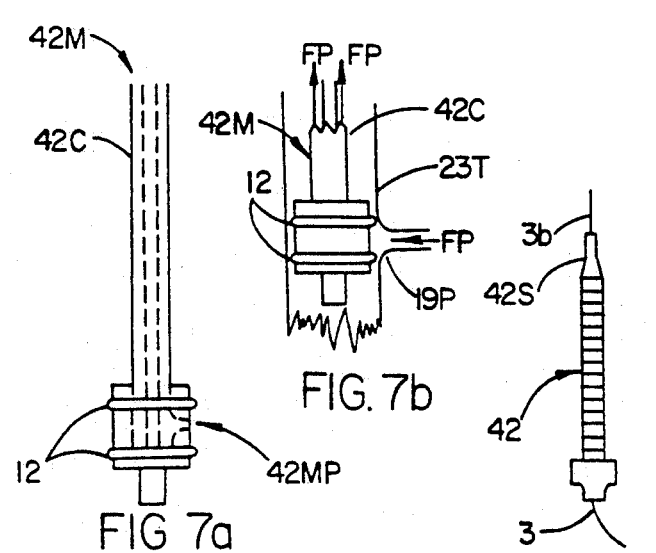
FIG 7a
FIG. 7b
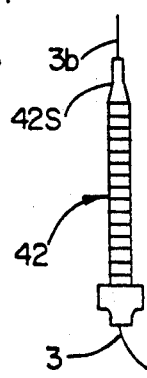
FIG 7c

DIRECT INJECTION MICRO NEBULIZER AND ENCLOSED FILTER SOLVENT REMOVAL SAMPLE INTRODUCTION SYSTEM, AND METHOD OF USE

This application is a continuation-in-part of pending U.S. patent application Ser. No. 07/813,766, filed Dec. 27, 1991, now U.S. Pat. No. 5,212,365.

TECHNICAL FIELD

The present invention relates to systems and methods for use in introducing samples to sample analysis systems, and more particularly to a small internal volume total consumption direct injection micro nebulizer sample introduction system, including nebulized sample desolvation and enclosed filter solvent removal systems.

BACKGROUND

The use of sample solution nebulizer systems to introduce liquid samples into sample analysis systems is well known. Sample solution nebulization is typically accomplished by known mechanical, pneumatic or ultrasonic nebulizer means for instance, and available sample analysis systems include Inductively Coupled Plasma (ICP), other plasma based systems, and mass spectrometers.

Typically, sample solution nebulization is carried out in an aerosol chamber at a location remote from a sample analysis system, and nebulized sample droplets must be transported to the location of the sample analysis system by way of a connection means. A common problem which occures during use is that nebulized sample is lost by adherence to the internal walls of the aerosol chamber and connection means between the output of the sample nebulizer system and the input to the sample analysis system. Additionally, the aerosol chamber and connecting means volume must be filled with nebulized sample to cause nebulized sample to eject from said connection means into the remotely located sample analysis system. A relatively larger amount of nebulized sample must then be prepared than would be the case if the sample nebulizer system had no aerosol chamber and was situated in closer proximity to the sample analysis system. System sensitivity is, as a result, adversely affected and tedious, time consuming, system flushing procedures are often required to prevent sample carryover from one analysis procedure from contaminating subsequent analysis procedure results. It would then, be very beneficial if a sample nebulizer system which did not require an aerosol chamber and which could be positioned closely adjacent to sample analysis systems were available.

In view of the identified problems, Fassel et al., designed a "micro nebulizer" system and obtained a Patent thereon in 1986, said Patent being No. 4,575,609. The Fassel et al. teachings are that the micro nebulizer should be inserted directly into a standard torch of the type used in Inductively Coupled Plasma sample analysis procedures, in which standard torch, during use, a plasma is formed. The micro nebulizer is designed to perform sample solution nebulization directly. That is, the aerosol chamber internal volume and connection means internal volume, between the sample nebulizer system and a remotely located sample analysis system, are eliminated.

The Fassel et al. invention assumes the presence of a first tube, which first tube is essentially the sample injector tube of a inductively coupled plasma standard torch. Briefly, to aid with understanding, said standard torch is comprised of a series of elongated concentric tubes, which concentric tubes are typically, but not necessarily, made of quartz. The centermost tube is typically termed the sample injector tube. It is typically circumscribed by an intermediate tube, which intermediate tube is typically circumscribed by an outer tube. One can visualize the torch system in side elevation, from a position perpendicularly removed therefrom, with the longitudinal dimensions of the various elongated tubes projecting vertically upward from an underlying horizontal surface. Sample particles from a typical sample nebulizing system are typically injected vertically into the sample injector tube of the standard torch from a sample access port at the vertically lower aspect thereof, and caused to flow through said sample injector tube to the upper aspect thereof under the influence of a pressure gradient, whereat they are ejected into the space above said upper aspect of the sample injector tube, which space is typically within the volume circumscribed by the outer tube of the standard torch system, in which space a plasma is typically created during use. As well, typically tangentially injected gas flows are entered into the annular spaces between the outer surface of the sample injector tube and the inner surface of the intermediate tube, and between the outer surface of the intermediate tube and the inner surface of the outer tube. (Note, tangential is to be understood to mean that a gas flow follows a spiral-like upward locus path from its point of entry to the standard torch). The typically tangentially injected gas flows are entered by way of intermediate and outer ports also present in the torch. Said typically tangentially injected gas flows serve to shield the various tubes which they contact from the intense temperatures and heat formed by creation of a plasma in the upper aspects of the torch, and to some extent aid sample flow into the plasma associated area.

The Fassel et al. invention teaches that rather than enter a previously, distally, nebulized sample to the sample access port of a standard torch, a micro nebulizer should be entered into the sample injector tube and positioned so that the upper aspect thereof is at an essentially equal vertical level with the upper aspect of the sample injector tube of the standard torch, into which the micro nebulizer is inserted. Sample solution is then entered into the micro nebulizer via a sample delivery inner tube, directly, without any prior sample nebulization being performed thereon. The Fassel et al. micro nebulizer is designed to cause sample solution entered thereto, to eject from the upper aspect of the micro nebulizer and thereby become nebulized. The upper aspect of the sample delivery inner tube thereof, is positioned at essentially the same vertical level as the upper aspect of the sample injector tube of the standard torch, hence, is located very near the position at which a plasma can be created for use in analysis of the ejected nebulized sample. It will be appreciated that the only nebulizer internal volume which exists is that within the micro nebulizer and the associated connection means thereto from the source of sample solution. Said internal volume is typically on the order of five (5) microliters and is orders of magnitude smaller than the internal volume associated with the sample injector tube of a standard torch and the connecting means thereto from a remotely located conventional sample solution nebulizer system.

To better understand the Fassel et al. micro nebulizer it is necessary to better describe the system thereof. Basically, the Fassel et al. micro nebulizer is comprised of an inner tube and an outer tube, which inner tube is concentrically circumscribed by said outer tube. The two concentric tubes are oriented vertically and placed into the first tube, which first tube can be thought of as the sample injector tube of a standard torch as described above. A sample solution of can be entered into the micro nebulizer at the lower aspect of the inner tube thereof and caused, under the influence of a pressure gradient, (typically 100 to 1000 psi), to flow vertically upward and eject from the upper aspect of the inner tube of the micro nebulizer. Sample solution velocities on the order of one-hundred (100) meters-per-second are common. In addition, a gas flow can be entered into the annular space between the outer surface of the inner tube and the inner surface of the outer tube of the micro nebulizer, which gas flow interacts with the sample solution flow at the point of its ejection from the inner tube of the micro nebulizer, thereby causing said sample solution to be nebulized by essentially pneumatic means. An additional gas flow can be injected into the annular space which results between the outer surface of the outer tube of the micro nebulizer and the inner surface of the sample injector tube of the standard torch into which the Fassel et al. micro nebulizer is inserted. Said additional gas flow can also aid with the sample solution nebulization effect. The nebulized sample solution then immediately injects into the space in the standard torch in which a plasma can be created. The disclosure of the Fassel et al. Patent teaches that a support tube should be epoxied to the outer surface of the outer tube of the micro nebulizer, along some portion thereof which is inside the first tube, (i.e. sample injector tube of the standard torch), during use, apparently to protect the outer and inner tubes thereof against being crushed when inserted into the sample injector tube of the standard torch, and to aid with a firm fit within the sample injector tube of the standard torch into which the micro nebulizer is inserted. The Fassel et al. disclosure teachings also indicate that the outer and inner tubes of the micro nebulizer should be attached to the standard torch by way of a fixed fitting, and that the upper aspect of the inner tube of the micro nebulizer should be positioned vertically at a level below the upper aspect of the sample injector tube of the standard torch. The drawings of Fassel et al. show that the upper aspect of said inner tube of the micro nebulizer is also placed vertically below the upper aspect of the outer tube of the micro nebulizer and that said outer tube of the micro nebulizer and the sample injector tube of the standard torch are tapered inwardly at their upper aspects. In use, it has been found, that the Fassel et al. system as described above, particularly when used with high solids content sample solutions, becomes clogged at the upper aspect thereof. This results in the necessity that the micro nebulizer be cleaned often, which cleaning is difficult to perform and often leads to breakage of the micro nebulizer. It has also been discovered that the upper aspect of the inner tube of the Fassel et al. system is difficult to position inside the outer tube of the Fassel et al. system, and that the Fassel et al. system tends dislodge from the point at which it is secured inside the standard torch sample injector tube at the lower aspect of said sample injector tube, when relatively high pressure gas flow is entered into the annular space between the outer surface of the outer tube of the micro nebulizer and the inner surface of the sample injector tube of the standard torch. It is emphasised that the securing of the micro nebulizer to the inside of the sample injector tube of the standard torch is by way of a fitting, through which fittinq is run the outer and inner tubes of the micro nebulizer.

The inventor in the present Application has found that great utility would result from major changes to the Fassel et al. system, which changes would provide means which allow a user thereof to:

1. easily access the inner portion of the upper aspect of the micro nebulizer; and
2. easily insert the inner tube of the micro nebulizer and adjust the vertical location of the upper aspect thereof independent from any interaction with the outer tube thereof.

Other improvements in the Fassel et al. system would result from use of a protective sleeve around at least a portion of the extent of the inner tube thereof, use of hydrofloric acid resistant nonmetalic materials in the construction thereof, and use of a unibody design for the basic portion of the micro nebulizer, which unibody design allows for connections at the lower, middle and upper vertical aspects thereof. The connection at the upper aspect thereof being to allow easy access and cleaning of accumulated sample solids, the connection at the lower aspect thereof being to allow inner tube upper aspect vertical level positioning, and the connection at the middle thereof being to allow attachment to a source of gas to cause a flow thereof into the annular space between the outer surface of the inner tube of the micronebulizer and the inner surface of outer tube thereof, which outer tube thereof would be formed by the unibody design of the micro nebulizer. The use of only nonmetalic materials is proposed to prevent untoward interaction with plasma energy which is common when metals are present near a plasma, and the use of hydrofloric resistant materials, (e.g. polyimides), is proposed to allow use of hydrofloric acid as a sample solvent.

Another very recent patent, No. 4,990,740 to Meyer, recognizes the benefits and problems associated with the Fassel et al. micronebulizer, and teaches an Intraspray ICP Torch which serves to overcome some of said problems. The Meyer invention, in essence, provides a low operational pressure equivalent to a micronebulizer system at the lower aspect thereof, and also provides a series of impactors thereabove in a torch system portion of the invention. The Meyer invention provides greater stability in both construction and in nebulized sample solution flow to an ICP. Said impactors serve to deflect large diameter droplets (e.g. over approximately fifteen (15) microns in diameter), and prevent their ejection from the upper aspect of the invention, and in addition to buffer the ejected flow of nebulized sample solution.

In view of the benefits provided by the Fassel et al. micro nebulizer, and in view of the difficulties associated with use thereof, which difficulties have received recognition from users thereof, there is thus demonstrated a need for an improved direct injection micro nebulizer.

Continuing, sample preparation for introduction to a sample analysis system typically involves not only a sample solution nebulization step, but also sample desolvation and solvent removal steps. Nebulized sample solution droplets are typically desolvated prior to being entered, for instance, to an ICP or MS. If this is not done, plasma instability and spectra emission interference can occur in plasma based analysis systems, and solvent outgassing in MS systems can cause pressures therein to rise to unacceptable levels.

Desolvation of sample solution droplets involves two processes. First, sample solution droplets are heated to vaporize solvent present and provide a mixture of solvent vapor and nebulized sample particles; and second, the solvent vapor is removed. The most common approach to removing solvent is by use of low temperature condenser systems. Briefly, in said low temperature condenser systems the nebulized sample solution droplets are heated to vaporize the solvent present, and then the resulting mixture of solvent vapor and nebulized sample particles is passed through a low temperature solvent removal system condenser. When the solvent present is water very high desolvation efficiency, (e.g. ninty-nine (99%) percent), is typically achieved, when the solvent condensing temperature is set to zero (0) to minus-five ($-5$) degrees centigrade. However, when organic solvents are present the desolvation efficiency at the indicated temperatures is typically reduced to less than fifty (50%) percent. Use of lower temperatures, (e.g. minus-seventy ($-70$) degrees centigrade), can improve the solvent removal efficiency, but will also cause greater loss of nebulized sample particles as an undesirable accompanying effect. In addition, low temperature desolvation systems typically comprise a relatively large volume condenser. This leads to sample "carry-over" problems from one analysis procedure to a subsequent analysis procedure as it is difficult to fully flush out the relatively large volume between analysis procedures.

A Patent to D'Silva, No. 5,033,541 describes a high efficiency double pass tandem cooling aerosol condenser desolvation system which has been successfully used to desolvate ultrasonically nebulized sample droplets. This invention presents a relatively small internal condenser volume, hence minimizes sample carry-over problems, however, while the invention operates at high desolvation efficiencies when water is the solvent involved, it still operates at lower desolvation efficiencies when organic solvents are used. The invention also requires sample passing therethrough to undergo turbulance creating direction reversals, and the use of relatively expensive refrigeration equipments. Turbulance in a nebulized sample flow path can cause reagglomeration of nebulized sample solution droplets and, especially when very low temperatures are present, recapture of nebulized desolvated sample particles present.

A Pat. to Skarstrom et al., No. 3,735,558 describes a counter-flow hollow tube(s) enclosed filter, mixed fluids key component removal system. Briefly, the invention operates to cause separation of key components from mixed fluids, such as water vapor from air, by entering the mixed fluid at one end of a single, or a series of, hollow tube(s), the walls of which are selectively permeable to the key components of the mixed fluid which are to be removed. A gas is entered to the system at the opposite end of the hollow tube(s), which gas is caused to flow over the outside of the hollow tube(s) in a direction counter to that of the mixed fluids, to provide an external purge of the key components of the mixed fluid which diffuse across the hollow tube(s). Diffusion of key components is driven by pressure and concentration gradients across the hollow tube(s). This approach to removal of diffusing components does not require the presence of low temperature producing refrigeration equipments, and presents a relatively small internal volume.

Two Pats. to Vestal, Nos. 4,958,529 and 4,883,958 also describe systems which utilize counter-flow enclosed filters systems, with the application being to remove solvent vapor from nebulized samples produced by a spraying technique. The vestal Patents state that the properties of the filter material used are not critical to the operation of the invention, but suggest the use of filter material available under the tradename of ZITEX. Said filter material provides a pore size of from two (2) to five (5) microns with a corresponding porosity of up to sixty (60%) percent. ZITEX is typically available in sheet form and enclosed filters made therefrom are typically constructed from a multiplicity of spacers and two sheets thereof. To provide an enclosed filter which is sufficiently long to provide reliable solvent vapor removal, in a reasonable space, it is typically necessary to arrange the spacers in a pattern which requires many severe sample flow path direction changes. A flow of solvent vapor and nebulized sample particles passing through such a tortuous pathway experiences turbulance. Turbulance causes sample to adhere and accumulate inside the enclosed filter thereby causing sample carry-over problems. The Vestal Patents also describe the heating of the enclosed filter to further assure continuous vaporization of solvent vapor present therein, and the flow of a gas outside the enclosed filter to remove solvent which diffuses through the enclosed filter.

The above presentation shows that the preparation of liquid samples for analysis in gas phase or particle analysis systems typically involves:

1. Nebulizing a sample solution to form sample solution droplets.
2. Desolvating the resulting nebulized sample solution droplets and removal of the solvent.
3. Transporting the sample through the nebulizing system, desolvation and solvent removal systems into a sample analysis system.
4. Doing the above with varying degrees of success as regards use with either water or organic solvents, minimizing sample carry-over from one analysis procedure to a subsequent analysis procedure and achieving long term stability of operation.

In view of the above it can be concluded that a sample introduction system which at once: provides high sample solution nebulization efficiency and aerosol conversion rate; provides more efficient, (e.g. more than ninty-nine and nine-tenths (99.9%) percent), desolvation of the produced nebulized sample solution droplets in a manner which is equally successful whether water or organic solvents are present; minimizes sample carry-over by increasing sample transport efficiency therethrough and which optimizes system long term operational stability, would be of great utility. Such a sample introduction system is taught by the present invention.

DISCLOSURE OF THE INVENTION

The objectives identified in the Background Section of this Disclosure are achieved by the present invention.

The present invention comprises a total consumption Direct Injection Micro Nebulizer System, which can be inserted into the space within a sample injector tube of a standard torch, as described with respect to the Fassel et al. invention in the Background Section of this Disclosure, or into specially designed torches which, for instance, have no sample injector tube present, to form a direct injection micro nebulizer based sample introduction and analysis systems. The present invention accepts a sample solution which has not been subject to prior nebulization and typically injects it into a closely situated plasma in a sample analysis system, performing required sample solution nebulization directly, again much as taught in the Fassel et al. Patent. The present invention, however, provides utility not taught in Fassel et al. and can be used in sample analysis systems other than those utilizing torches and plasmas, as it does not require the presence of an ICP torch sample injector tube as part of its construction.

The present invention is, in its preferred embodiment, comprised of a system of a primary body element, a top element, a double nut element system, or functionally equivalent sample delivery tube system adjustment means, and a sample delivery tube which is typically encompassed within a separate or integral protective sleeve over at least a portion of its length, to form the sample delivery tube system.

The primary body element of the present invention is preferably, but not necessarily, of unibody construction and is generally elongated in shape with a distinct longitudinal dimension, and with a centrally located longitudinally oriented hole extending therethrough. At the upper aspect of the primary body element, as it is viewed in side elevation from a position perpendicularly removed therefrom, with the longitudinal dimension thereof projecting vertically upward, perpendicular to an underlying horizontal surface, is located a first connection means, which first connection means typically comprise female screws threads. (Note that the direct injection micro nebulizer need not be oreinted as just described to facilitate discussion, during use). A top element, which has a centrally located longitudinally oriented hole therethrough and which has connection means which are complimentary to said first connection means at the upper aspect of the primary body element, is also typically present and removably attached to the primary body element by way of said connection means. The top element can be of an elongated design which provides means for positioning the upper aspect of the top element near a plasma in an inductively coupled plasma torch, while maintaining an attached primary body element of the direct micro injection nebulizer system at some distance therefrom. The top element can also have a saphire or functionally equivalent, ultraviolet transparent, non-heat conducting, high strength, tight tolerance inner diameter top element tip component present at its upper aspect. In addition, a circumscribing tube can be present which forms an annular space around the top element, through which annular space a gas of a desired temerature can be caused to flow, via a modified top element port, during use. The purposes of the top element tip component and the circumscribing tube include allowing effecting better transport of sample through the total consumption direct injection micro nebulizer during use, hence, reducing sample deposition and accumulation, (i.e. clogging etc.), problems. At the lower aspect of the primary body element there is present a second connection means, again comprising, typically, female screw threads. A double nut element system, or functionally equivalent sample delivery tube system adjustment means, which has a centrally located longitudinally oriented hole therethrough and which has connection means thereon, which connection means are complimentary to the second connection means at the lower aspect of the primary body element, is also present and removably attached to the primary body element by way of said second connection means. In one embodiment of the present invention a chromatography column can be attached to the sample delivery tube system, typically at the lower aspect of the sample delivery tube system adjustment means, to allow temporal preseparation of sample components in a multi-analyte component sample solution prior to entry thereof into the direct injection nebulizer system. (Note, a chromatography column causes various analyte components in a sample solution to move therethrough, as the containing sample solution is passed therethrough, at varying rates based upon, for instance, varying affinities for the various components by the materials present in the chromatography column.) In another embodiment of the present invention the sample delivery tube system adjustment means is fixed and adjusted only at manufacture or during iniatial user utilization. Also present on said primary body element is a third connection means which provides access to the centrally located longitudinally oriented hole which projects through the primary body element.

The sample delivery tube of the present invention is typically but not necessarily, over at least the portion of its length extending from the lower aspect of the sample delivery tube system adjustment means, encompassed within a separate or integral protective sleeve, and the combination sample delivery tube and optional protective sleeve, (or in some cases only the sample delivery tube per se), forming a sample delivery tube system, is threaded into the centrally located longitudinally oriented hole through the double nut element system, or functionally equivalent sample delivery tube system adjustment means. The sample delivery tube per se, (i.e. the sample delivery tube system without a protective sleeve), is then, typically, threaded through the centrally located longitudinally oriented hole through the primary body element, then into and out of the centrally located longitudinally oriented hole through the top element, when said top element is present. The top element, when present, is then removably attached to the primary body element by way of the connection means thereon which are complimentary to the first connection means present at the upper aspect of the primary body element. It should be noted that inserting the sample delivery tube into the centrally located longitudinally oriented hole which extends through the top element prior to removably attaching it to the upper aspect of the primary body element at the first connection means thereon facilitates the direct injection micro nebulizer system construction process. At the lower aspect of the direct injection micro nebulizer system the sample delivery tube system is removably attached to the primary body element, via the upper oriented nut of the double nut element system, or functionally equivalent sample delivery tube system adjustment means, by way of the second connection means present at the lower aspect of the primary body element. The lower nut of the double nut element system firmly grips the sample delivery tube system, and removably attaches to the upper nut of the double nut element, or functionally equivalent sample delivery tube system adjustment means, system by way of connection means thereon. It should be understood that the vertical level of the upper aspect of the sample delivery tube can then be easily adjusted by a user of the present invention by manual or automated manipulation of the upper nut of the double nut element system, or functionally equivalent sample delivery tube system adjustment means which has not been fixed in position, where it removably attaches to second connection means at the lower aspect of the primary body element of the direct injection micro nebulizer system taught herein.

During use with a standard torch and plasma sample analysis system, the present invention, as described above, is inserted into and secured within, the space within the sample injector tube of a standard torch, or within the intermediate tube of a specially designed torch which has no sample injector tube present for instance, such that the upper aspect of the sample delivery tube is positioned, typically, just below the position therein at which a plasma can be created for use in the analysis of samples. The vertical level of the upper aspect of the sample delivery tube can be precisely adjusted by manipulation of the double nut element system, or sample delivery tube system adjustment means functional equivalent, as alluded to above. A sample solution is entered into the sample delivery tube, at the end thereof opposed to that present at the upper aspect of the present invention. Said sample solution is forced to move through the sample delivery tube and eject from the upper aspect thereof. Said flow is typically effected by a pressure gadient, but can also be effected by application of an electrical gradient. In addition, a gas flow is caused to be entered to the third connection means on the primary body element. Said gas flow, under the influence of a pressure gradient, transverses the length of the primary body element in the annular space between the outer surface of the sample delivery tube and the inner surface of the centrally located longitudinally oriented hole through primary body element. At the upper aspect of the primary body element, or the upper aspect of the top element if present, said gas flow is ejected from from the annular space between the outer surface of the sample delivery tube and the inner surface of the centrally located longitudinally oriented hole.

The ejected sample solution interacts with said ejected gas flow to effectively nebulize the sample solution into sample solution droplets. In addition, an auxilary sample gas flow can be entered into the annular space between the outer surface of the primary body element of the present invention, and the inner surface of the sample injector tube of the standard torch, if present, by way of an access port in the standard torch. Specially designed top elements can include a circumscribing tube and modified top element port to allow a similar effect in torches which have no sample injector tube present. Said gas flow, again typically under the influence of a pressure gradient, will eject from the annular space into which it is entered, and interact with the simultaneously ejected sample solution, and optionally, a gas flow as described above which is entered to the third connection means of the primary body element. The overall effect being to provide finely nebulized sample solution droplets, and cause same to be vertically swept into the region of the standard, or specially designed, torch in which a plasma can be created. If a specially designed torch which has no sample injector tube present is used, the additional gas flow just described, will of course, not be possible but can be approximated if the modified top element alluded to above is present. This arrangement is better described in the Detailed Description Section herein.

The present invention additionally, in the preferred embodiment thereof, is fabricated from hydrofloric acid resistant nonmetallic materials, and the primary body element is firmly but removably secured within the sample injector tube of the standard, or intermediate tube of a specially designed, torch with which it is used, by means of one or more "O" rings which circumscribe the primary body element. As well, an essentially tubular shaped, strength providing, top element tip component which provides a tight tolerance inner diameter, is transparent to microwave radiation, not susceptible to heating and which is resistant to sample deposition and accumulation during use, can be present at the upper aspect of a top element. A typical top element tip component will be constructed from saphire tubing or functional equivalent.

It will be appreciated that the present invention allows a user thereof to easily access the inner space at the upper aspect of the primary body element when the top element is removed. This feature allows easy cleaning of any solid sample build up at said location which might clog the invention. In addition, threading the sample delivery tube into the centrally located longitudinally oriented hole through the top element, when it is present, can be easily performed when the top element is removed from the first connection means at the upper aspect of the primary body element. Also, as alluded to above, the vertical level of the upper aspect of the sample delivery tube can be easily and precisely adjusted by manipulation of the upper nut element of the double nut system, or by manipulation of a sample delivery tube system adjustment means which is not fixed in position, at its attachment to the second connection means on said primary body element. In some embodiments, however, the sample delivery tube adjustment means is adjusted only during manufacture or during initial user utilization. That is, a sample delivery tube can be permanently fixed in place by a plug-like, (which can be a fused double-nut system), element which is firmly secured at the lower aspect of the primary body element, which plug-like element firmly grips the sample delivery tube and fixes it in relationship to the primary body element.

While the use of a standard or specially designed torch, such as typically used in Inductively Couples Plasma analysis of samples was used as an example in the above, it is to be understood that the present invention could also be used to introduce sample into, for instance, a mass spectrometer sample analysis system, perhaps by way of a desolvation chamber and/or solvent removal system. In such a system momentum separators, skimmers, enclosed filters, roughing pumps and ion focusing lenses etc. might be present. That is to say the present invention can be used with sample analysis systems which require sample nebulization, other than sample analysis systems which utilize standard or specially designed ICP torches and plasmas.

The present invention teaches use of desolvation and enclosed filter solvent removal systems, and the properties of the enclosed filter material composition have been found to be of importance to the operation thereof. The enclosed filter is made from a material which allows the solvent vapor to diffuse therethrough, but which retains the nebulized sample particles therein. In the preferred embodiment of the present invention the material is GORE-TEX, (GORE-TEX is a tradename), micro porous PTFE tubing, manufacturer part No. X12323, No. X12499 or No. X12500. Said GORE-TEX microporous PTFE tubing has inner diameters of approximately four (4), two (2) and one (1) millimeters respectively. Said GORE-TEX microporous tubing filter material is preferred as it simultaneously provides high porosity (e.g. seventy (70%) percent) and small pore size, (e.g. one (1) to two (2) microns). The higher the porosity of a material, the easier it is for solvent vapor to diffuse therethrough, and the smaller the pore size of a material, the smaller the nebulized sample particles can be and still be retained within an enclosed filter made thereof as they are transported therethrough. It is difficult to obtain both high porosity and small pore size in a filter material, but said combination has been achieved in the GORE-TEX product and use of same allows shorter length enclosed filters to be used which provide excellent solvent vapor removal characteristics. It should be apparent that a shorter enclosed filter length provides a smaller enclosed volume inside said enclosed filter, and that translates into a reduced chance for nebulized sample particles to adhere to and accumulate within same during use at reasonable sample flow rates therethrough. The Present invention operates quite well when the enclosed filter length is fourty (40) centimeters or less in length. Said enclosed filter length is five (5) or more fold shorter than enclosed filters providing equivalent desolvation capability which are made from other materials, (e.g. filter material available under the tradename of ZITEX for instance). Continuing, the solvent vapor which diffuses across the enclosed filter is flushed out of the system, typically by a flow of gas outside the enclosed filter, while the nebulized sample particles are transported into a sample analysis system, typically under the influence of the pressure gradient which is created by entering sample and nebulization gas flows to the direct injection micro nebulizer, perhaps in conjunction with an additional nebulized sample transport enhancing entered, (typically in a tangentially oriented spiral locus manner), gas flow. Note, however, that it is within the scope of a modified embodiment of the present invention to remove solvent vapor which diffuses through the enclosed filter by use of a cold temperature condenser through which the enclosed filter extends rather than by way of a flow of gas outside the enclosed filter. If this is done the enclosed filter is maintained at a temperature above the vaporization point of the solvent involved to prevent solvent condensation and sample analyte deposition and accumulation inside the enclosed filter. The cold temperature condenser is, however, maintained below the condensation point of the solvent present. Also, if this is done the pressure gradient which drives the nebulized sample particles transport will typically be created, at least partially, by use of vacume pumps which reduce pressure at the outlet, sample analysis end of the enclosed filter. The injected nebulization gas flow, mentioned above will be minimized and additional nebulized sample transport enhancing gas flows will not be present. Continuing, when a solvent removal gas flow outside the enclosed filter is used to remove diffused solvent vapor the flow rate thereof is typically on the order of tenths-of-a-liter-per-minute when the sample nebulization gas flow is set to a mililiter-per-minute level and when the sample solution flow into the direct injection micro nebulizer is set to a microliter-per-minute level. With said parameters the solvent vapor partial pressure difference across the enclosed filter membrane is kept to an optimum level by quickly removing solvent vapor which diffuses across the enclosed filter membrane. In addition, it must be understood that it is important to keep the enclosed filter temperature above the boiling point of the solvent involved to prevent condensation of solvent vapor therein. When water is used as a solvent the temperature is typically kept at one-hundred-and-twenty (120) degrees Centigrade or above.

It is also mentioned that use of solvents with boiling points well below the temperature at which a sample of interest evaporates serves to optimize operation of the present invention, and that the present invention is equally effective in desolvating water or organically solvated samples.

The present invention will be better understood by reference to the Detailed Description Section of this Disclosure and the accompanying drawings.

SUMMARY OF THE INVENTION

The use of sample solution nebulizer systems to prepare samples for analysis is well known. Typically a sample solution is subjected to aerosol chamber contained pneumatic, mechanical or ultrasonic processes, for instance, which cause a sample solution to be nebulized at a location distally situated from a sample analysis system, such as an inductively coupled plasma or mass spectrometry sample analysis system. As a result the nebulized sample must be transported to the sample analysis system through a relatively large internal volume connection means. The aerosol chamber and connection means internal volume is the source of numerous problems. For instance, its presence dictates that a relatively large amount of nebulized sample solution be available to fill same. The sensitivity of the overall sample analysis system is thus reduced. Additionally, said internal volume must often times be flushed out after an analysis procedure to prevent contamination of results obtained in subsequent analysis procedures.

In view of the above identified problems inventors have developed and Patented a Micro Nebulizer for Direct Injection of Samples to a sample analysis system. See Pat. No. 4,575,609 to Fassel et al. Said Micro Nebulizer is, during use, placed, and performs nebulization, very near associated sample analysis equipment, which in the case of the Fassel et al. invention involves placement in the sample injector tube of an inductively coupled plasma sample analysis system standard torch. The internal volume of the micro nebulizer is, as a result, kept very small, typically on the order of five (5) microliters. The overall effect is that the sensitivity of an overall system using the Fassel et al. micro nebulizer is increased and the "carry-over" of sample from one sample analysis procedure to a subsequent sample analysis procedure is easier to prevent because there is less internal volume to flush out between analysis procedures.

Users of the Fassel et al. micro nebulizer have found, however, that certain design features thereof make it inconvenient to use. For instance it is difficult to clean the device without completely breaking it down, and it is difficult to adjust the upper aspect of the inner tube, which inner tube carries a sample solution flow, with respect to the upper aspect of the outer tube thereof. It is noted that the annular space between the outer surface of the inner tube and the inner surface of the outer tube provides a pathway through which a gas flow is maintained during use of the micro nebulizer. Said gas flow interacts with the sample solution flow at the location at which both flows simultaneously eject from the upper aspect of the micro nebulizer to cause the sample solution to be nebulized into sample solution droplets. The two flows alluded to, it will be appreciated, must eject at proper orientations with respect to one another or proper sample solution nebulization is not achieved. The utility of an ability to easily manually or automatically adjust the vertical location of the upper aspect of the inner tube with respect to that of the outer tube should then be appreciated. It has also been found that the inner tube of the Fassel et al. invention can be easily crushed, for example when the invention is being cleaned. A separate or integral protective sleeve which covers at least a portion thereof would therefore provide utility. Additionally, it is taught herein that the major element of the direct injection micro nebulizer system should preferably be of one piece unibody construction, should contain no metallic parts and be of a material which is resistant to degradation by hydrofloric acid. The later design points are related to the occurance of untoward effects when the invention is placed near an inductively coupled plasma, and to the fact that samples to be nebulized at times are solvated by a solvent containing hydrofloric acid or the fact that hydrofloric acid is sometimes used as a cleaning agent in analysis systems.

In addition, the present invention provides that the direct injection nebulizer system should be designed to allow use with not only standard ICP torch sample analysis systems, but also with ICP torches which have no sample injector tube present or with other sample analysis systems such as mass spectrometer sample analysis systems. That is, the direct injection micro nebulizer system should not require attachment to the sample injector tube of a standard ICP torch tto be utilized.

An improved micro nebulizer system, termed a Direct Injection Micro Nebulizer System, is thus taught herein, which serves to overcome the problems inherent in the use of the Fassel et al. invention.

Continuing, often a sample solution is introduced to a sample analysis system by way of sample nebulizing, desolvating and solvent removal systems. The use of pneumatic and mechanical means to nebulize sample solutions and the use of low temperature condensers to remove solvent from resulting nebulized sample solution droplets, which have been heated to vaporize the solvent present, is generally taught. Such desolvating and solvent removal systems, however, are generally not as efficient when an organic solvent is present, as compared to when water is the solvent.

Various References teach the use of relatively small volume enclosed filters which allow solvent vapor to diffuse therethrough, but which retain nebulized sample particles which result from the desolvation of nebulized sample solution droplets, therein. Said references do not, however, emphasise that the properties of the material from which an enclosed filter is fabricated, or enclosed filter geometry are critical to system performance. In addition, no known reference teaches that high efficiency total consumption direct injection micro nebulizer systems can, or should, be used in conjunction with relatively small volume high efficiency enclosed filter solvent removal systems to form a sample introduction system.

The present invention provides a sample introduction system which combines a highly efficient total consumption direct injection micro nebulization system with a highly efficient, essentially geometrically linear, relatively small internal volume, enclosed filter solvent removal system. In use nebulized sample droplets formed by the total consumption direct injection micro nebulizer are desolvated by being subjected to heat in a desolvation system and are caused to be transported through the enclosed filter solvent removal system to an analysis system. Solvent vapor diffuses through the enclosed filter and is removed, typically, by a flow of gas outside said high efficiency enclosed filter. In some applications a low temperature condenser, (rather than a solvent removal gas flow outside the enclosed filter), through which the enclosed filter passes, might be used to condense and remove said diffused solvent vapor, while the enclosed filter temperature is maintained above the boiling point of the solvent involved. This might be done, for instance, when a mass spectrometer analysis system is used with the present invention.

The relatively small volume enclosed filter solvent removal system is, in the preferred embodiment, comprised of small diameter tubing (e.g. one (1) to four (4) milimeters), fabricated from high porosity, small pore size material, typically GORE-TEX, (GORE-TEX is a tradename), Micro porous PTFE tubing. As a result the present invention provides an efficient sample nebulization system in conjunction with a solvent removal system which minimizes sample carry-over from one analysis procedure to subsequent analysis procedures, said carry-over being associated with relatively large desolvation condenser volumes, and even relatively small volume enclosed filter solvent removal systems which make use of inferior filter materials and/or relatively tortuous sample flow path enclosed filter geometries. The present invention also provides a system which does not cause nebulized sample particle recapture during desolvation and solvent removal. This is the result of maintaining the enclosed filter temperature above the boiling point of the solvent involved. It is also emphasized that the ddesolvation system of the present invention works equally well with water or organic based solvents.

It is therefore a purpose of the present invention to provide a direct injection micro nebulizer system which is easy to clean.

It is another purpose of the present invention to provide a direct injection micro nebulizer system in which adjustment of the vertical location of the upper aspect of the inner, sample delivery, tube with respect to the outer tube, (termed a primary body element in the present invention), is, in the preferred embodiment, easy to carry out.

It is yet another purpose of the present invention to teach a direct injection micro nebulizer system which is constructed from nonmetalic and/or hydrofloric acid resistant materials.

It is still yet another purpose of the present invention to teach a direct injection micro nebulizer system which provides one piece or unibody construction of the major element, the primary body element, of the invention.

Still yet another purpose of the present invention is to teach the optional use of a separate or integral protective sleeve on the sample delivery, (i.e. inner tube of Fassel et al. invention), tube to form a crush resistant sample delivery tube system.

Yet still another purpose of the present invention is to teach a direct injection micro nebulizer system which can be used in sample analysis systems which do not provide a sample injector tube of a standard ICP torch as an element thereof.

It is yet another purpose of the present invention to provide a system for introducing samples to sample analysis systems which utilizes efficient sample nebulization means.

Yet another purpose of the present invention to provide a system for introducing samples to sample analysis systems which utilizes efficient nebulized sample solution droplet desolvation and solvent removal means.

It is yet another purpose of the present invention to provide a system for introducing samples to sample analysis systems which minimizes sample carry-over from one sample analysis procedure to a subsequent analysis procedure.

It is still yet another purpose of the present invention to provide a system for introducing samples for entry to sample analysis systems which efficiently transports sample therethrough.

It is another purpose of the present invention to provide a system for introducing samples to sample analysis systems which is equally efficient in desolvating nebulized sample solution droplets whether water or organic solvents are present.

It is still yet another purpose of the present invention to provide a system for introducing samples to sample analysis systems which demonstrates stable operation and long component lifetimes.

BRIEF DESCRIPTION OF THE DRAWINGS

FIG. 1a shows a side elevational view of one embodiment of the present invention in cross section, as viewed from a position perpendicularly removed therefrom.

FIG. 1b shows a perspective view of a portion of a sample delivery tube system of the present invention.

FIG. 2 shows a side elevational view of a standard torch used in inductively coupled plasma analysis of samples, with the present invention present in the sample injector tube thereof, viewed from a position perpendicularly removed therefrom.

FIG. 3 shows a portion of the present invention oriented horizontally in cross section, with block diagrams representing sample analysis system elements other than an inductively coupled plasma standard torch.

FIG. 4 shows a side elevational view of a modified embodiment of the present invention in cross section, as viewed from a position perpendicularly removed therefrom.

FIG. 5 shows a side elevational view of a specially designed torch used in inductively coupled plasma analysis of samples, with the modified embodiment of the present invention present within the intermediate tube thereof, viewed from a position perpendicularly removed therefrom.

FIG. 6 shows a modular sample injector tube system which can be placed in the specially designed torch of FIG. 5 in place of the modified embodiment of the present invention of FIG. 4 when it is desired to utilize sample solution nebulizing means located distally from the sample analysis system.

FIG. 7a shows an alternate embodiment of a top element in which a circumscribing tube provides an annular space through which a gas can be caused to flow during use to aid sample flow through the direct injection micronebulizer.

FIG. 7b shows a partial view of the top element of FIG. 7a placed into a torch with a port present thereon which allows entering a gas flow into the annular space identified in FIG. 7a.

FIG. 7c shows a modified embodiment of a top element which includes a top element tip component. Said top element tip component provides high strength, is ultraviolet transparent, is not prone to heating when positioned near a plasma, provides tight tolerance inner diameter, and is less prone to being clogged by sample during use.

DETAILED DESCRIPTION

Figure 8:
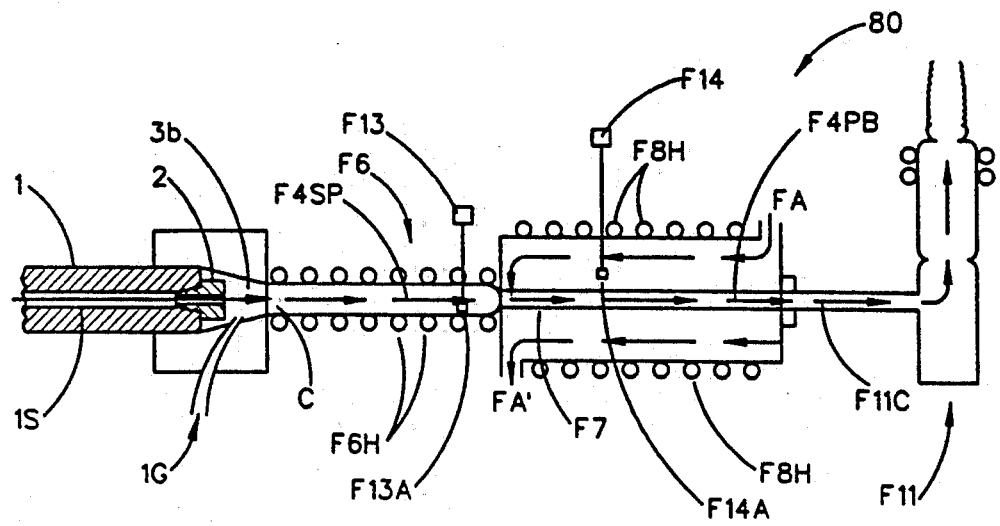
FIG. 8 shows a a partial view of a direct injection micronebulizer in combination with desolvation and enclosed filter solvent removal systems. The enclosed filter solvent removal system utilizes a gas flow outside the enclosed filter to sweep away diffusing solvent vapor.

Turning now to the drawings, there is shown in FIG. 1a one embodiment of the present invention (10), in cross sectional elevation as viewed from a position perpendicularly removed therefrom with the longitudinal dimension thereof projecting vertically upward from an underlying horizontal surface. In particular note that there is shown a primary body element (1), typically of unibody construction, a top element (2), a double nut element system (11) comprised of upper nut (6) and lower nut (7), a sample delivery tube system (3) typically comprised of a sample delivery tube (3b) and a protective sleeve (3a), and an "O" ring (12). FIG. 1b shows an enlarged view of a portion of the sample delivery tube system (3) in perspective, showing that the sample delivery tube system (3) can be comprised of a sample delivery tube (3b) and a protective sleeve (3a) through which the sample delivery tube (3b) is threaded, over at least a portion of its length. Said protective sleeve (3a) serves to protect the sample delivery tube (3b) against being crushed. (It is mentioned that a high strength crush resistant sample delivery tube (3b) per se could alone comprise a sample delivery tube system (3) with the protective sleeve (3a) being an integral component thereof, or a sample delivery tube per se could, alone, form the sample delivery tube system). It is also possible to provide sample delivery tube system (3) with a temperature control element such as an ohmic high resistance electrical conducting coil wound therearound along at least a portion of its length, (similar to the shown protective sleeve (3a)), so that during use of the direct injection micro nebulizer (10) in a sample analysis procedure the temperature of said sample delivery tube system (3) can be controlled. Controlling the temperature thereof can lead to a decreased tendency of sample solids to adhere to and deposit inside the sample delivery tube (3b) during use. As a result a lessened chance that the sample delivery tube system (3) will become clogged is achieved. It is noted that the sample delivery tube (3b) is typically fifty (50) micrometers inner diameter and one-hundred-eighty (180) micrometers outer diameter. As well, the primary body element (1) is typically approximately one-hundred (100) milimeters in length. These dimensions are exemplary and not limiting, however.

Continuing, note that the top element (2), primary body element (1) and upper and lower nuts (6) and (7) respectively have centrally located longitudinally oriented holes therethrough, through which the sample delivery tube system (3), or at least the sample delivery tube (3b) per se can be threaded. (Note, the term "centrally located" is to be taken to mean that when the various elements of the present invention are properly attached to one another, the longitudinally oriented holes through them line up with one another so as to provide a continuous hole through the assembled direct injection micro nebulizer system). It is noted that the inner diameter of the centrally located longitudinally oriented hole through the top element (2) is typically, but not necessarily, two-hundred (200) micrometers. As a result the annular space between the outer surface of the sample delivery tube and the inner surface of the centrally located longitudinally oriented hole through the top element (2), when the sample delivery tube (3b) is threaded therethrough, is only approximately ten (10) micrometers radially. Also note that the primary body element (1) has, at its upper aspect, a first connection means (4), typically comprised of female screw threads, which first connection means interacts with complimentary connection means on the lower aspect of top element (2) to removably attach top element (2) to said primary body element (1). The primary body element (1) also provides a second connection means (5), at the lower aspect thereof, typically female screw threads, which second connection means (5) interact with complimentary connection means on the upper aspect of upper nut (6) of the double nut system (11), to removably attach upper nut (6) to the lower aspect of the primary body element (1). The lower aspect of the upper nut (6) provides connection means (8), typically female screw threads, which connection means interact with complimentary connection means at the upper aspect of the lower nut (7) to removably attach said second nut (7) to said first nut (6). The primary body element also presents a third connection means (9), typically female screw threads which allows attachment thereof to a source of gas flow, which gas flow is identified as "G" in FIG. 2. Said third connection means (9) provides access to the centrally located space of the centrally located longitudinally oriented hole which is present through the primary body element (1), which space is designated (1S), by way of access port (9p).

It is to be understood that sample delivery tube system (3) is caused to be typically firmly, but removably, secured to the lower nut (7) of the double nut element system (11). This is typically accomplished by providing a tapering female screw thread connection means at the lower aspect of the upper nut (6), into which complimentary connection means, comprising male screw threads at the upper aspect of the lower nut (7), can screw. As the complimentary connection means are caused to be screwed into the connection means (8) at the lower aspect of the upper nut (6), the centrally located hole through lower nut (7) is caused to collapse to some extent and firmly grasp said sample delivery tube system (3). It is also to be understood that the second connection means (5) at the lower aspect of the primary body element (1) allows complimentary connection means at the upper aspect of upper nut (6) to be manipulated with respect to the second connection means (5) on primary body element (1), so that the vertical location of the upper aspect of sample delivery tube (3b) can be precisely adjusted, when the sample delivery tube (3b) is threaded through the entire direct injection micro nebulizer system as shown in FIG. 1a. Said manipulation typically comprises turning of upper nut (6) with respect to primary body element (1), although any functionally equivalent system can be used. It is also noted that it is within the scope of the present invention to provide a sample delivery tube adjustment means in the form of a fixed retaining element at the second connection means (5) on primary body element (1). Said double nut system might be locked, (or the double nuts might be fused into a plug-like element, or replaced by a plug-like element), in a desired position at manufacture, or by a user during initial utilization, to form a fixed sample delivery tube adjustment means, (or retention), system. In addition, the second connection means might be a separate or integral plug in the primary body element, with a simple hole therein, through which simple hole the sample delivery tube is passed, and secured. The claims are to be interpreted to include such sample delivery tube adjustment means and retention systems under the terminology "sample delivery tube adjustment means". That is, the only "adjustment" possible might be during manufacture of the present invention, or by a single or a few initial actions by a user, or any functional equivalent thereto.

It should be also appreciated that the first connection means (4) at the top of primary body element (1) allows a user of the present invention to easily gain access to the upper aspect of the space (1S) within the primary body element (1) by removal of top element (2). This allows easy threading of sample delivery tube (3b), and easy cleaning of any sample solids which might accumulate within the space (1S) of the primary body element (1) during use in a sample analysis procedure. Said sample solids accumulation would, for instance, occur if the upper aspect of the sample delivery tube (3b) were not threaded through the longitudinally oriented centrally located hole in the top element. This would configure the system very much like the system shown in the Fassel et al. patent drawings. It is noted, however, that the preferred arrangement of the present invention provides that the upper aspect of the sample delivery tube (3b) be threaded through the centrally located longitudinally oriented hole which transverses the top element (2).

The preferred materials from which the present invention is constructed are hydrofloric acid resistant and nonmetallic. This is important as some sample solids are solvated in solvent containing hydrofloric acid, and metals can interact with energy fields when the direct injection micro nebulizer is placed into an inductively coupled plasma analysis system, discussed below with respect to FIG. 2. Said interaction can cause untoward effects.

Turning now to FIG. 2, there is shown a side elevational view, as viewed from a position perpendicularly removed therefrom, of a vertically oriented standard torch (20) used with Inductively Coupled Plasma sample analysis systems. The present invention direct injection micro nebulizer (10) is shown placed therein. Note the presence of an outer tube (21), intermediate tube (22) and sample injector tube (23), as well as an outer port (16), intermediate port (17), auxiliary sample flow port (19) and a sample injector port (23p). When the standard torch (20) is used without the present invention (10) present therein, a nebulized sample flow is entered via the sample injector port (23p), and caused, typically under the influence of a pressure gradient, to flow vertically through the sample injector tube (23) and eject into the space above the vertically upper aspect of the sample injector tube, which space is designated as (25), at which location a plasma is typically caused to exist during use. Vertically or tangentially directed gas flows "A" and "B" are entered at the outer and intermediate ports (16) and (17) respectively, and under the influence of pressure gradients move upward through the spaces of the standard torch (20) into which they are injected. Typically tangentially directed flows are used In which the gas follows a vertically upward spiral-like motion. The purposes of said injected gas flows "A" and "B" are to shield the components of the standard torch (20), (e.g. (21), (22) and (23)), which they contact against the temperature and heat produced by a created plasma, and to aid the sample entry flow into said plasma. It is mentioned that normally the auxiliary sample flow port (19) will not be present when the standard torch (20) is used without the present invention (10) present therein.

Now, FIG. 2 shows the present invention (10) as inserted into the space within the sample injector tube (23) of the standard torch (20). In use the typically tangentially injected gas flows "A" and "B" at outer and intermediate ports (16) and (17) respectively will again be injected for purposes similar to those described above With the present invention (10) present, however, a sample solution flow "C" is entered into the sample delivery tube system (3) and caused to flow through the length of said sample delivery tube system (3), and eject from the vertically upper aspect thereof, (shown as sample delivery tube (3b) per se in the Figures), into the space (25) of the standard torch (20) in which a plasma can be created. Note it is also possible to induce sample flow by application of an electric potential between the upper and lower extents of the sample delivery tube, said voltage constituting a functionally equivalent pressure gradient. Such an interpretation is to be considered within the scope of the claims. Also note that the sample solution flow "C" is not nebulized prior to entry to the sample delivery tube (3b). In addition, a gas flow "G" is injected into port (9p) of the primary body element (1) and caused to flow through the annular space (1S) within the centrally located longitudinally oriented hole which vertically transverses the primary body element, between the outer surface of the sample delivery tube system (3) and the inner surface of the centrally located longitudinally oriented hole through the primary body element (1), and out thereof between the annular space between the outer surface of the sample delivery tube (3b) and the inner surface of the longitudinally oriented centrally located hole which is present through the top element (2). Interaction of the sample solution flow "C" and the gas flow "G" where both eject from the vertically upper aspect of the present invention causes nebulization of the sample ssolution to occur. Said nebulization can be aided by injection of an auxiliary sample gas flow "F" at auxiliary sample port (19) of the standard torch (20), which gas flow "F" ejects from the annular space between the outer surface of the primary body element (1) of the present invention and the inner surface of the sample injector tube (23) of the standard torch (20) and helps further nebulize, and to sweep, the nebulized sample flow created by interaction of flows "C" and "G" upward into space (25) of the standard torch (20).

Also note the presence of an "O" ring (12) around the outer surface of primary body element (1). Said "O" ring (12) serves to firmly secure the present invention (10) inside the sample injector tube of the standard torch (20).

Turning now to FIG. 3, there is shown a partial view of the present invention (10), oriented with the longitudinal dimension thereof projecting horizontally so that top element (2) is at the right of the primary body element (1) in said figure. Also shown are blocks (31) and (32). Said blocks represent, generally, elements of sample analysis systems other than those that use inductively coupled plasmas and standard torches, such as desolvation systems and mass spectrometers or any other analytical instruments including those which involve sample deposition and/or optical sample analysis methods. The claims are to be interpreted so as to include use of the presently disclosed direct injection micro nebulizer sample introduction invention with any sample analysis system, and in orientations wherein the longitudinal dimension of the direct injection micro nebulizer is other than than vertical. The terms, "vertical", "upper", "top" etc., hence, are used herein only to facilitate disclosure and description. Additional discussion of sample desolvation and solvent removal systems is found with respect to FIGS. 8 through 11.

Finally, as regards FIGS. 1 and 2, the double nut element system (11) of the present invention is a sample delivery tube system adjustment means and demonstrates one approach by which the vertical level of the upper aspect of the sample delivery tube system (3) can be easily and conveniently adjusted without the requirement that the present invention system be dismantled. Any functionally equivalent sample delivery tube system adjustment means, either repeatably adjustable or only adjustable at manufacture or one or a few times by a user etc., is to be considered as within the scope of the claims. In addition, either manual or automated adjustment of the sample delivery tube system position during use, are within the scope of the claims.

Turning now to FIGS. 4 and 5, there is shown a modified embodiment of the present direct injection micro nebulizer system and torch. FIG. 4 shows a direct injection micro nebulizer system (40) which is functionally similar to that described with respect to FIG. 1*a*, but with design modifications present. Generally, primary body element (41) provides first, second and third connection means (44), (45) and (49) respectively. Top element (42) attaches to first connection means (44) as does top element (2) attach to first connection means (4) in FIG. 1, but top element (42) has present an elongated portion, (e.g. approximately seventy (70) milimeters long), which is not present in top element (2). In addition it is noted that the primary body element (41) is typically, but not necessarily, approximately one-hundred (100) milimeters long and approximately fifteen (15) milimeters outer diameter at the point at which it enters a torch as shown in FIG. 5. Reference to FIG. 5 shows that the elongated portion of top element (42) allows positioning sample delivery tube (3*b*) which threads therethrough near the location (55) in torch (50) where a plasma can be formed during use, without positioning the vertically upper aspect of primary body element (41) near thereto. Also shown in FIG. 4 are upper nut (46) and lower nut (47), the system of which allows easy adjustment of the vertical level of the upper aspect of the sample delivery tube (3*b*). Upper nut (46) attaches to second connection means (45) of the primary body element (41), and lower nut (47) attaches to the upper nut (46) by means of connection means (48). Sample delivery tube system (3) is firmly gripped by lower nut (47), and adjustment of the connection between the primary body element (41) and the upper nut (46) allows easy adjustment of the vertical level of the upper aspect of the sample delivery tube (3*b*). (Note that previously discussed fixed sample delivery tube system adjustment means might also be applied in the presently discussed embodiment). Third connection means (49) allows attachment to a source of gas flow shown as "G" in FIG. 5. Interaction between sample flow "C" and gas flow "G" where both simultaneously eject from the upper aspect of top element (42) causes sample nebulization. Note that FIG. 5 shows a torch (50) which does not have a sample injector tube analogous to sample injector tube (23) in FIG. 2. As a result there is no provision for a gas flow analoqous to gas flow "F" shown in FIG. 2. The torch of FIG. 5 secures the primary body element (41) of the present invention within intermediate tube (52) by way of "O" rings (12), which "O" rings are typically present as a pair thereof. The outer tube (51) is analogous to outer tube (21) of FIG. 2 and ports (56) and (57) are analogous to ports (16) and (17) in FIG. 2. Gas flows "A" and "B" are similar in both FIGS. 5 and 2. It is noted that when the torch (50) is used. It is possible to remove the direct injection micro nebulizer (40) therefrom and insert a separate sample injector tube assembly. FIG. 6 shows a modular sample injector tube system (60) with substitute primary body element (41*p*) and sample injector tube (42*p*) present. This allows easy convertability of the torch from one which uses the present invention to one which allows use of sample nebulized by other (e.g. pneumatic, ultrasonic etc.) means at a distal location. The torch embodiment (50) of FIG. 5 is therefore termed a "demountable torch" which is suitable for use with a direct injection micro nebulizer system.

FIG. 5 shows lower nut (47), (or what could be a fixed position equivalent), as being coupled to a chromatography column (59). when this, or equivalent, configuration is present, a sample solution "C" entered to the sample delivery tube (3*b*) will typically contain multi-analyte components. The chromatography column (59) will cause temporal separation of the various analyte components in a solution passed therethrough, based upon differing transport characteristics of each analyte component in the chromatography column. As a result, a single sample analysis procedure might be able to identify a sequence of sample analyte components very easily and conveniently. Chromatography, it is mentioned, is a well known technique for providing a means for separating sample analyte components in a multi component sample solution as said sample solution is passed through a chromatography column.

FIG. 7*a* shows, on an enlarged scale, a view of a modified top element (42*m*), which modified top element (42*m*) is similar to the top element (42) shown in FIG. 4, but has an additional top element circumscribing tube (42*c*) present. Said top element circumscribing tube (42*c*) serves to form an annular space surrounding the upper aspect of top element (42) through which annular space a gas of a desired temperature can be flowed during use, which flow of gas aids sample flow out of the sample delivery tube. Said gas flow being entered via modified top element port (42*mp*). Note that modified top element port (42*mp*) has "O" rings (12) positioned with respect thereto so that they can form an encompassing seal when said modified top element (42*m*) is placed into, for instance, an ICP torch such as demonstrated in FIG. 2. FIG. 7*b* shows a partial view of a modified top element (42*m*) placed into a portion of an ICP torch tube (23*t*). Modified top element port (19*p*) allows entry of a gas flow "FP" which gas flow exits through the above identified annular space. (Note that gas flow "FP" and modified top element port (19*p*) serve somewhat analogous purposes to gas flow "F" and auxilliary sample flow port (19) shown in FIG. 2 wherein a torch with a sample injector tube is represented). "O" rings (12) are shown providing a seal between the modified top element (42*m*) and the ICP torch tube (23*t*) so that gas flow "FP", entered to port (19*p*), is directed into and through modified top element (42*m*) as shown. FIG. 7*c* shows yet another modification to a top element, (e.g. (42) or (42*m*)), in the form of an additional top element tip component (42*s*) at the uppermost extent thereof, as said top element is oriented in FIG. 7*c*. Note that sample delivery tube (3*b*) extends through the top element tip component (42*s*). Said top element tip component (42*s*) is typically tubular in shape and made of saphire or a functional equivalent. Said top element tip component (42*s*) is typically one (1) to ten (10) milimeters long and provides a tight tolerance inner diameter centrally oriented longitudinally directed hole therethrough. The purposes of the top element tip component (42*s*) include provision of a high strength, ultraviolet transparent, non-heat conducting component upon which sample is not prone to deposit and accumulate during use. During use top element (42) can be subject to abundant ultraviolet radiation by being placed near a plasma discharge. The presence of top element tip component (42*s*) helps to overcome adverse effects, such as invention clogging brought abount by the effects of said ultraviolet radiation on the top element.

Turning now to FIGS. 8 and 10, there are shown components which can be added to the direct injection nebulizer system to form the desolvated sample particle sample introduction system of the present invention. When desolvation of nebulized sample solution droplets produced by the direct injection micro nebulizer system is desired, they can be caused to flow into a desolvation chamber (F6) where they are subjected to a temperature in excess of the vaporization temperature of the solvent involved by heater means (F6H). The resulting mixture of solvent vapor and nebulized sample particles (F4Sp) can then be caused to flow, typically under the influence of the pressure gradient created by entering sample flow "C" and carrier gas flow "G", (see FIGS. 2 and 5 for flows "C" and "G"), into an enclosed filter, (see (F7) or (C7) in FIGS. 8 and 10 respectively), of solvent removal system (80) or (90). FIG. 8 also shows the optional presence of an additional gas flow "IG" which can be entered near the outlet of the direct injection micro nebulizer (1) sample deliery tube (3) to aid nebulized sample flow "C". Said gas flow "IG" will typically be injected so as to flow tangentially, (i.e. in a spiral locus essentially parallel to the injected nebulized sample "C" flow). Heater means (F8H) or (C48H) serve to keep the temperature in the solvent removal system (80) or (90) above the boiling point of the solvent present. Typical temperatures maintained within the solvent removal means are in the range of fourty (40) and onehundred-and-fifty (150) degrees centigrade, depending on the solvent being used.

Enclosed filter (F7), (or (C7)), is made of a material which allows solvent vapor to diffuse therethrough, but which retains nebulized sample particles therein. It is to be understood that a solvent vapor removing gas flow "FA" is caused to enter solvent removal system (80) at inlet port (F8a), (see FIG. 9), flow around the outside of enclosed filter (F7), and exit at outlet port (F8b). Said solvent vapor removing gas flow is indicated as "FA" at the inlet port (F8a) and as "FA'" at the outlet port (F8b). Said solvent vapor removal gas flow serves to remove solvent vapor which diffuses through said enclosed filter (F7). The nebulized sample particles (F4SP) which remain inside of enclosed filter (F7) are then caused to flow, typically under the influence of the above identified pressure gradient, into an Inductively Coupled Plasma analysis system, or other analysis system (F11) by way of connection means (F11C). Said flow is identified by the numeral (F4PB).

It is mentioned that enclosed filter (F7) or (C7) is typically made of tubular PTFE material and is available under the tradename of GORE-TEX. Said material has a pore size of one (1) to two (2) microns and a porosity of seventy (70%) percent. Tubular forms of the filter are available with one (1), two (2) and four (4) milimeter inner diameters and are identified as GORE-TEX micro porous tubings. Said microporous tubular filters are especially suitable for use in the present invention. The GORE-TEX PTFE material has been found to provide the present invention with improved operating characteristics by allowing a relatively short length, (e.g. less than fourty (40) centimeters), of enclosed filter to be used, while still allowing efficient removal of solvent vapor. Enclosed filters made of other commercially available materials must typically be five (5) or more fold longer to provide equivalent solvent removal capability. A shorter length of enclosed filter means that the enclosed filter contains a smaller volume and, hence, that sample "carry-over" from one analysis procedure to a subsequent analysis procedure is greatly reduced. In addition, said enclosed filter, being of essentially linear geometry or at worst requiring only gradual curves therein to fit into reasonably sized system containments, does not present a sample transported therethrough with turbulance creating severe direction reversals. Longer enclosed filters made from inferior pore size and porosity parameter filter materials typically do include such turbulence creating sample flow path direction reversals. The result is increased sample deposition therein and "carry-over" based problems during use.

Also shown in FIG. 8 are desolvation chamber and solvent removal system thermocouples (F13A) and (F14A) respectively, and associated heating controllers (F13) and (F14) respectively. Said elements monitor and control of the temperatures in the associated invention system components.

Figure 9:
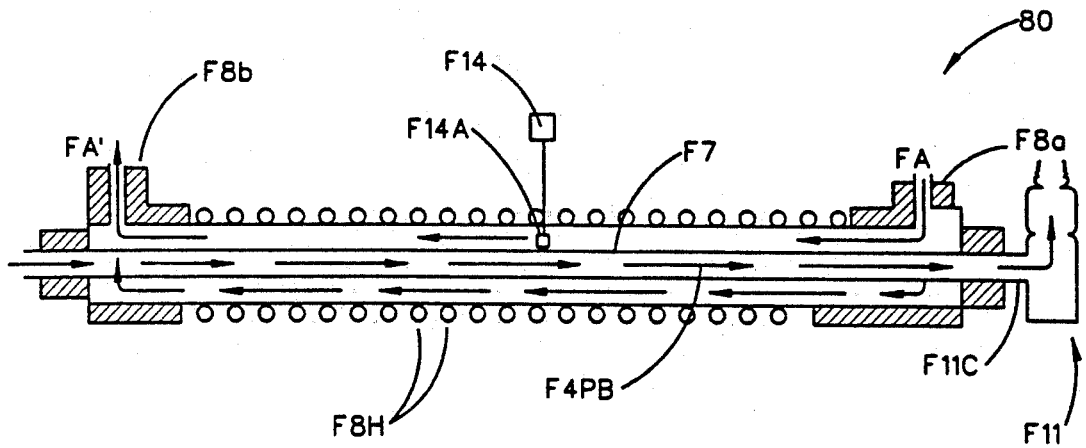
FIG. 9 shows an expanded view of the solvent removal system shown in FIG. 8.

Turning now to FIG. 9, there is shown an expanded diagramatic view of a solvent removal system (80). Note in particular the inlet port (F8a) at which solvent removal gas flow "FA" is entered, and outlet port (F8b) at which solvent vapor gas flow "FA'" exits. While the solvent removal system (80) can be of any functional geometry, the preferred embodiment is a tube of approximately one-half (0.5) inch in diameter, or less. Said shape and size provides an effective volume flow rate therethrough when a typical one (1) liter per minute solvent vapor removal gas flow "FA"-"FA'" is entered thereto. It is preferred to cause solvent vapor removal gas flow "FA"-"FA'" to flow in the direction as shown because the relative solvent saturation of the gas in solvent vapor removal gas flow "FA"-"FA'" along its locus of flow, is closely matched to the that of the solvent vapor inside the enclosed filter (F7). However, solvent vapor removal gas flow could be caused to flow in a direction opposite, (e.g. "FA'"-"FA"), to that shown and be within the scope of the present invention. Also shown in FIG. 2 are heater element (F8H), nebulized sample particles flow (F4PB) and connection means (F12) to partially shown inductively coupled plasma or other sample analysis system (F11). It is also mentioned that it is within the scope of the present invention to utilize a chemical desicant or a dry gas in solvent vapor removal gas flow "FA"-"FA'" or "FA'"-"FA'".

It is also mentioned that while distinct elements are shown and described for performing various described functions in the present invention, it is within the scope of the present invention to perform more than one function in one element of the overall system of the present invention, or to combine various elements of the overall system into composite elements. For instance, desolvation chamber (F6) and solvent removal system (80) might be combined into one system.

It will be appreciated, in view of the above, that the present invention provides a small internal volume enclosed filter (F7) in which solvent vapor is filtered away from nebulized sample particles (F4PB), the volume inside a one (1) to four (4) milimeter inner diameter GORE-TEX tube essentially comprising said enclosed filter volume. As a result, sample carry-over problems are minimized. In addition, the presently discussed embodiment of the present invention system (80), it is emphasized, does not require low temperatures to condense solvent vapor. Low temperatures can cause loss of nebulized sample particles (F4PB) by way of recapture by condensing solvent vapor in systems which utilize condensers. Also, the present invention can be operated to provide high solvent removal efficiency by control of desolvation chamber (F6) and solvent removal system (80) temperatures in conjunction with other system parameters, regardless of solvent type, (e.g. water, organic etc.). This is considered a very important point. The first embodiment of the present invention, thus, provides a sensitive, sample conserving, highly efficient system for providing highly nebulized sample particles and transporting them to a plasma or other analysis system.

It is also to be understood that while the desolvation chamber (F6) and solvent removal system (80) are each shown as being single units in the drawings, it is possible for each to be comprised of multiple sequential units.

Figure 10:
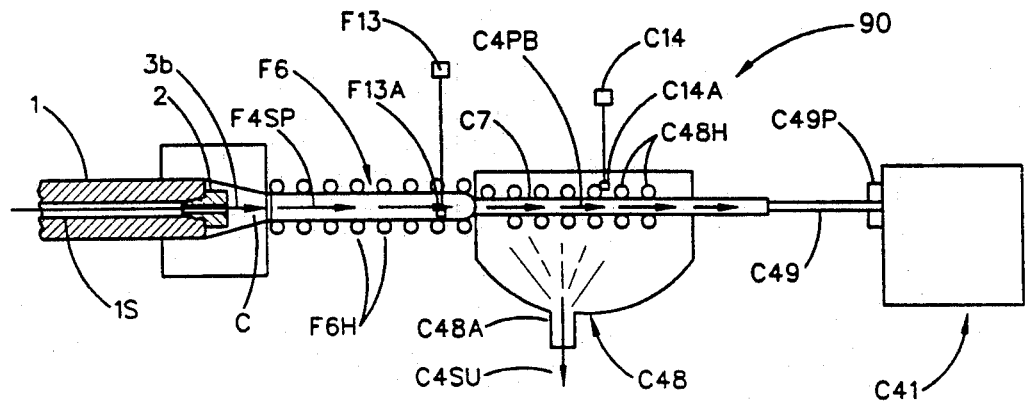
FIG. 10 shows a partial view of a direct injection micronebulizer in combination with desolvation and enclosed filter solvent removal systems. The enclosed filter solvent removal system utilizes a cold temperature condensor arrangement to remove diffusing solvent vapor.
Figure 11:
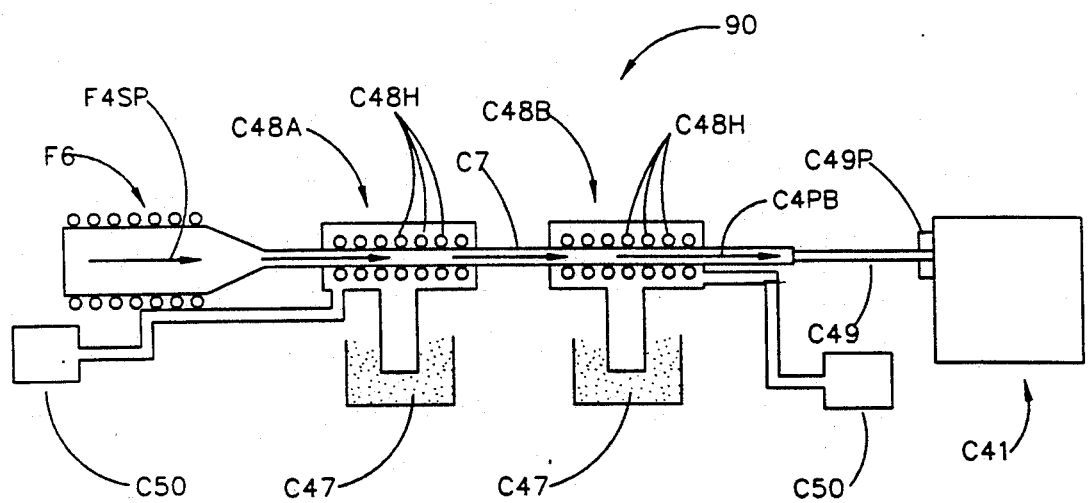
FIG. 11 shows an expanded of view one embodiment of a cold temperature solvent removal system as shown in FIG. 10.

Turning now to FIG. 10, there is shown a diagramatic view of a modified embodiment of the present direct injection micro nebulizer, desolvation and enclosed filter solvent removal sample introduction invention (90). The discussion relating to FIG. 8 is equally valid to point at which the mixture of solvent vapor and desolvated sample particles (C4PB) enters the solvent removal system. Note that FIG. 10, however, shows a cold temperature condenser solvent removal system (90) with an enclosed fiilter (C7) therethrough, and with heating elements (C48H) present around the enclosed filter (C7). Entering solvent vapor is maintained at a temperature above the boiling point of the solvent as it is transported through the enclosed filter, by said heating elements (C48H), to the point along the enclosed filter at which it diffuses through the enclosed filter and into a cold temperature condensor (C48), in which the solvent vapor condenses and flows out of drain (C48A), said flow being indicated by (C4SU). Entering nebulized desolvated sample particles (C4PB) are transported toward an analysis system (C41) by way of connection means (C49) from the solvent removal system, and connection means (C49P) at the analysis system (C41). Analysis system (C41) is typically, when this modified embodiment of the present invention is used, a mass spectrometer which operates at a very low internal pressure, (e.g. ten-to-the-minus-fifth Torr). At connection means (C49P) the pressure is typically approximately one (1) Torr. The pressure at the direct injection micro nebulizer sample delivery tube (3b) is typically seven-hundred-sixty (760) torr or greater. The driving force for sample transport through the nebulization and enclosed filter solvent removal system (90) is thus identified. Note, however, that gas flow "IG" as can be used in the embodiment of FIG. 8, is typically not present in the embodiment of FIG. 10. The additional pressure differential provided by the application of low pressure at the sample analysis system typically provides sufficient nebulized sample "C" flow transport driving force without said additional gas flow "IG". Turning now to FIG. 11, there is shown an expanded exemplary diagramatic view of the solvent removal system (90) in FIG. 10. Note that two sections (C48A) and (C48B) are shown. This is shown as an example only, and it is within the scope of the present invention to provide a solvent removal system with more or less than two sections, just as other elements of the present invention can be of other than exactly shown functional construction. Also shown in FIG. 11 are vacume pumps (C50) and cold temperature maintaining liquid, typically liquid nitrogen or a mixture of dry ice and isopropanol (C47). It is specifically noted that the modified embodiment of the present invention shown in FIGS. 10 and 11, can be termed a Universal Particle Beam Interface for use in interconnecting liquid chromatography and mass spectrometer systems. Connection means (C49) can be a one-sixteenth (1/16) inch diameter tube, which will easily attach to most mass spectrometer systems without modification thereto.

It is also to be understood that the desolvation and solvent removal systems of the primary and modified embodiments of the present invention can be, in certain rare cases where desolvation of sample solution droplets is not desired, eliminated. The overall systems of FIGS. 8 and 10 depict such an additional embodiment of the present invention when the desolvation and solvent removal systems are visualized as inactive sample outlet means which can be connected to sample analysis systems (F11) or (C41). This would essentially be the case were the desolvation and solvent removal systems not operated during a sample preparation procedure.

It is to be understood that while inductively coupled plasma and mass spectrometers were used as examples herein, any gas phase or particle sample analysis system is to be considered equivalent for the purpose of claim interpretation.

It is also to be understood that sample solutions can originate from any source and can be subjected to component separation steps prior to being entered into a system for introducing samples as sample flows. This might be the case, for instance, where the sample solution is derived from a liquid chromatography source.

Finally, it must be emphasised that the direct injection micro nebulizer was defined herein with terminology appropriate when it is viewed with the longitudinal dimension thereof projecting vertically as shown in FIGS. 1, 2, 4, and 5. Terms such as "vertically", "top", "lower" and "upper" were used to describe elements and gas and sample flow directions etc. with reference to said Figures. To avoid confusion, the terms assigned elements of the direct injection micro nebulizer in discussion of FIGS. 1, 2, 4 and 5 were not changed when discussing the systems in FIGS. 3, 8, 9, 10 and 11. That is, for instance, "top element" was not redefined to be a "side element". As a result, claim language is to be read to include an interpretation of the words "vertical" and "upward" etc. as meaning "horizontal" and "sidewise" etc. when appropriate. Stated otherwise, the right side of the page upon which are FIGS. 3, 8, 9, 10 and 11 should be considered to be the top thereof when necessary. Claims to systems in FIGS. 8, 9, 10 and 11 should be read in this light.

Having hereby disclosed the subject matter of this invention, it should be obvious that many modifications, substitutions, and variations of the present invention are possible in light of the teachings. It is therefore to be understood that the invention may be practised other than as specifically described, and should be limited in breadth and scope only by the claims.

I claim:

1. A direct injection micro nebulizer sample introduction system comprising a direct injection micro nebulizer, said direct injection micro nebulizer comprising:
a primary body element,
a sample delivery tube system,
a sample delivery tube system adjustment means,
and said direct injection micro nebulizer sample introduction system further comprising;
a nebulized sample solution droplet desolvation system, and
an enclosed filter solvent removal system;
said primary body element being of a generally elongated shape presenting with a longitudinal dimension, and said primary body element having a first connection means at the upper aspect thereof, with upper aspect being defined as the vertically higher end of the primary body element as viewed in side elevation from a position perpendicularly removed therefrom while the longitudinal dimension thereof projects vertically upward and perpendicular to an underlying horizontal surface; said primary body element also having a second connection means at the lower aspect thereof and a third connection means thereon;
said sample delivery tube system comprising at a minimum a sample delivery tube;
said sample delivery tube system adjustment means being connected to the primary body element at the second connection means thereof;
said primary body element and sample delivery tube system adjustment means having centrally located longitudinally oriented holes therethrough;
said sample delivery tube system being threaded into the centrally located longitudinally oriented hole in the sample delivery tube system adjustment means and through the centrally located longitudinally oriented hole through the primary body element so that the upper aspect of the sample delivery tube is near the upper aspect of the primary body element;

the position of the upper aspect of the sample delivery tube system being precisely adjustable by manipulation of the sample delivery tube system adjustment means;

said sample delivery tube allowing a sample solution to be entered thereto at a lower aspect thereof and forced to flow through said sample delivery tube to the vertically upper aspect thereof;

said third connection means on the primary body element allowing a gas flow to be entered into and forced to flow through the annular space between the outer surface of the sample delivery tube and the inner surface of the centrally located longitudinally directed hole through the primary body element;

such that during use said sample solution flow and said gas flow are simultaneously ejected from the upper aspects of the sample delivery tube and the annular space between the outer surface of the sample delivery tube and the inner surface of the centrally located longitudinally directed hole through the primary body element respectively and interact with one another such that the sample solution is caused to be nebulized into droplets;

said nebulized sample solution droplet desolvation system being connected to the direct injection micro nebulizer, at one extent of said sample solution droplet desolvation system, and said enclosed filter solvent removal system being connected at an opposite extent thereof;

to said nebulized sample solution droplet desolvation system and enclosed filter solvent removal system nebulized sample solution droplets can be entered during use; said nebulized sample solution droplet desolvation system serving to vaporize solvent from entered nebulized sample solution droplets and said enclosed filter solvent removal system serving to remove said vaporized:

solvent which diffuses through the enclosed filter, to provide nebulized sample particles inside the enclosed filter which can be transported into a sample analysis system.

2. A direct injection micro nebulizer sample introduction system as in claim 1, in which the solvent removal system utilizes a flow of gas outside the enclosed filter to remove solvent vapor which diffuses through the enclosed filter.

3. A direct injection micro nebulizer sample introduction system as in claim 1, in which the solvent removal system utilizes a low temperature condenser to condense and remove solvent vapor which diffuses through the enclosed filter.

4. A solvent removal system for separating solvent vapor from a mixture of desolvated nebulized sample particles formed by entering a sample solution to a nebulizer and desolvation system combination system during the use thereof, which solvent removal system comprises an enclosed filter, which enclosed filter is made from tubular PTFE material, through which tubular PTFE material solvent vapor entered to the internal space thereof can diffuse, but which tubular PTFE enclosed filter retains likewise entered desolvated nebulized sample particles of a diameter larger than a micron or so, inside thereof.

5. A solvent removal system as in claim 4, in which the nebulize is a direct injection micro nebulizer system.

6. A desolvated sample particle sample introduction system which comprises a direct injection micro nebulizer in combination with nebulized sample droplet desolvation and solvent removal systems, which solvent removal system comprises an enclosed tubular filter made of PTFE.

7. A direct injection micro nebulizer sample introduction system as in claim 1, which further comprises a top element, said top element having a centrally located longitudinally oriented hole therethrough and said top element attaching to the first connection means of the primary body element by way of complimentary connection means thereon, and said sample delivery tube being threaded through the centrally located longitudinally oriented hole in said top element so that the upper aspect thereof is positioned near the upper aspect of the top element, and said gas flow which passes through the annular space between the outer surface of the sample delivery tube and the inner surface of the centrally located longitudinally oriented hole through the primary body element ejects from the annular space between the outer surface of the sample delivery tube and the inner surface of the centrally located longitudinally oriented hole through the top element; which top element can have affixed, at its upper extent, a length of top element tip component tubing that provides a tight tolerance inner diameter hole therethrough, and which is made from a material with the properties of being essentially transparent to ultraviolet radiation, not subject to heating when subjected to plasma discharge, and resistant to sample deposit and build-up thereon during use; and which top element can also have a circumscribing tube present which provides an annular space between the top element and said circumscribing tube, which annular space is accessible through a modified top element port, through which annular space a gas can be caused to flow during use to aid sample flow out of the sample delivery tube system.

8. A direct injection micro nebulizer sample introduction system as in claim 1, in which the primary body element is made from hydrofloric acid resistant nonmetallic material.

9. A direct injection micro nebulizer sample introduction system as in claim 1, which further comprises a chromatography column which is attached to the sample delivery tube system, through which chromatography column a sample solution flows prior to flowing through the sample delivery tube inside the primary body element.

10. A direct injection micro nebulizer sample introduction system as in claim 1, in which the sample delivery tube system includes, along at least a portion of its length, a temperature control element for use in controlling the temperature thereof.

11. A direct injection micro nebulizer sample introduction system as in claim 1, in which the first, second and third connection means of the primary body element comprise female screw threads.

12. A direct injection micro nebulizer sample introduction system as in claim 7, in which the top element and the sample delivery tube system adjustment means are attached to the primary body element at the first and second connection means thereof respectively in a manner which allow easy removal thereof.

13. A direct injection micro nebulizer sample introduction system as in claim 1, in which the first connection means of the primary body element is simply the upper aspect of the longitudinally directed centrally located hole through said primary body element.

14. A direct injection micro nebulizer sample introduction system as in claim 1 in which the sample delivery tube system adjustment means comprises a double nut system, with the first nut thereof having connection means complimentary to the second connection means of the primary body element, and the second nut thereof having connection means thereon which are complimentary to additional connection means in the first nut thereof and means for firmly securing the sample delivery tube system such that when the two nuts are connected to one another, and the combination is connected to the primary body element at the second connection means thereof, adjustment of the first nut connection in the second connection means of the primary body element causes the upper aspect of the sample delivery tube to be adjusted with respect to the longitudinal dimension of the primary body element.

15. A direct injection micro nebulizer sample introduction system as in claim 1 in which the sample delivery tube adjustment means is a fixed element which is attached to the lower aspect of the primary body element, allowing adjustment of the location of the upper aspect of the sample delivery tube only at manufacture or at initial user utilization, and which sample tube adjustment means supports the sample delivery tube with respect to the primary body element.

16. A method of introducing sample to a sample analysis system which comprises:
   a. obtaining a direct injection micro nebulizer sample introduction system comprising a direct injection micro nebulizer, said direct injection micro nebulizer comprising:
   a primary body element,
   a sample delivery tube system,
   a sample delivery tube system adjustment means,
   and said direct injection micronebulizer sample introduction system further comprising;
   a nebulized sample solution droplet desolvation system, and
   an enclosed filter solvent removal system;
   said primary body element being of a generally elongated shape presenting with a longitudinal dimension, and said primary body element having a first connection means at the upper aspect thereof, with upper aspect being defined as the vertically higher end as the primary body element is viewed in side elevation from a position perpendicularly removed therefrom while the longitudinal dimension thereof projects vertically upward and perpendicular to an underlying horizontal surface; said primary body element also having a second connection means at the lower aspect thereof and a third connection means thereon;
   said sample delivery tube system comprising at a minimum, a sample delivery tube;
   said sample delivery tube system adjustment means being connected to the primary body element at the second connection means thereof;
   said primary body element and sample delivery tube system adjustment means having centrally located longitudinally oriented holes therethrough;
   said sample delivery tube system being threaded into the centrally located longitudinally oriented hole in the sample delivery tube system adjustment means upward and through the centrally located longitudinally oriented hole through the primary body element so that the upper aspect of the sample delivery tube is near the upper aspect of the primary body element;
   the position of the upper aspect of said sample delivery tube system being precisely adjustable by manipulation of the sample delivery tube adjustemnt menas;
   said sample delivery tube allowing a sample solution to be entered thereto at a lower aspect thereof and forced to flow through said sample delivery tube to the upper aspect thereof;
   said third connection means on the primary body element allowing entry of a gas flow into and through the annular space formed between the outer surface of the sample delivery tube and the inner surface of the centrally located longitudinally directed hole through the primary body element;
   such that during use said sample solution flow and said gas flow are simultaneously ejected from the upper aspects of the sample delivery tube and the annular space between the outer surface of the sample delivery tube and the inner surface of the centrally located longitudinally directed hole through the primary body element respectively and interact with one another such that the sample solution is caused to be nebulized into droplets;
   said nebulized sample solution droplet desolvation system being connected to the direct injection micro nebulizer, at one extent of said sample solution droplet desolvation system, and said enclosed filter solvent removal system being connected at an opposite extent thereof;
   to said nebulized sample solution droplet desolvation system and enclosed filter solvent removal system nebulized sample solution droplets can be entered during use; said nebulized sample solution droplet desolvation system serving to vaporize solvent from entered nebulized sample solution droplets and said enclosed filter solvent removal system serving to remove said vaporized solvent which diffuses through the enclosed filter, to provide nebulized sample particles inside the enclosed filter which can be transported into a sample analysis system for analysis by a detector therein,
   b. entering a sample solution to the sample delivery tube at the lower aspect thereof and causing said sample solution to flow to the upper aspect of said sample delivery tube and eject therefrom while simultaneously entering a gas flow into the third connection means on the primary body element and causing it to flow through the annular space between the outer surface of the sample delivery tube and the inner surface of the centrally located longitudinally oriented hole through the body element and eject from the upper aspect of said annular space, thereat interacting with the simultaneously ejected sample solution flow in a manner which causes the solution to become nebulized into droplets;
   c. causing said nebulized sample solution droplets to enter the nebulized sample solution droplet desolvation system wherein they are heated to a temperature above the boiling point of the solvent present to form a mixture of nebulized sample particles and solvent vapor;
   d. causing said mixture of nebulized sample particles and solvent vapor to enter the solvent removal system wherein said solvent vapor diffuses through the walls of the enclosed filter; and e. causing the nebulized sample particles which remain inside the enclosed filter to flow into a sample analysis system.

17. A method of introducing sample as in claim 16 which further comprises the step of affixing a top element to the direct injection micro nebulizer, said top element having a centrally located longitudinally oriented hole therethrough and said top element being attached to the first connection means of the primary body element by way of complimentary connection means thereon, and said sample delivery tube being threaded through the centrally located longitudianlly oriented hole through said top element so that the upper aspect thereof is positioned near that of the upper aspect of said top element, and said gas flow which passes through the annular space between the outer surface of the sample delivery tube and the inner surface of the centrally located longitudinally oriented hole through the primary body element ejects from the annular space between the outer surface of the sample delivery tube and the inner surface of the centrally located longitudinally oriented hole through the top element.

18. A method of introducing sample as in claim 17 which further includes the step of introducing a flow of gas into an annular space formed by a circumscribing tube which is present around said top element.

19. A method introducing sample as in claim 16 which further comprises the step of utilizing a flow of gas outside the enclosed filter to remove solvent vapor which diffuses through the enclosed filter.

20. A method of introducing sample as in claim 16 which further comprises the step of utilizing a low temperature condenser to condense and remove solvent vapor which diffuses through the enclosed filter.

21. A method of introducing sample into a sample analysis system which comprises the steps of:
 a. obtaining a direct injection micro nebulizer sample introduction system comprising a direct injection micro nebulizer, a nebulized sample solution droplet desolvation system and an enclosed filter solvent removal system;
 said direct injection micro nebulizer comprising means for entering a sample solution and a gas flow such that interaction therebetween causes said sample solution to become nebulized into sample solution droplets;
 said nebulized sample solution droplet desolvation system providing means for desolvating said nebulized sample solution droplets to form a mixture of nebulized sample particles and solvent vapor; p1 said enclosed filter solvent removal system providing means for removal of said solvent vapor which diffuses therethrough;
 said direct injection micro nebulizer being attached to said nebulized sample solution droplet desolvation system at one extent thereof, and said enclosed filter solvent removal system being attached to said nebulized sample solution droplet desolvation system at another extent thereof such that sample solution entered to the direct injection micro nebulizer can be nebulized into nebulized sample solution droplets and said nebulized sample solution droplets can be caused to flow into said nebulized sample solution droplet desolvation system, and desolvated nebulized sample particles can be caused to flow into said solvent removal system;
 b. entering sample solution and a gas flow to the direct injection micro nebulizer;
 c. causing formed nebulized sample solution droplets to flow into the nebulized sample solution droplet desolvation system in which said nebulized sample solution droplets are desolvated to form a mixture of nebulized sample particles and solvent vapor;
 d. causing said mixture of nebulized sample particles and solvent vapor to flow into said solvent removal system; and
 e. removing solvent vapor which diffuses through the enclosed filter and causing nebulized sample particles which remain inside said enclosed filter to flow into a sample analysis system.

22. A method of introducing sample as in claim 21 which further comprises the step of utilizing a flow of gas outside the enclosed filter to remove solvent vapor which diffuses through the enclosed filter.

23. A method of introducing sample as in claim 21 which further comprises the step of utilizing a cold temperature condensor to condense and remove solvent vapor which diffuses through the enclosed filter.

24. A direct injection micro nebulizer system comprising:
 a primary body element, and
 a sample delivery tube system,
  said primary body element being of a generally elongated shape presenting with a longitudinal dimension, and said primary body element having a first connection means at the upper aspect thereof, with upper aspect being defined as the vertically upper end as the primary body element is viewed in side elevation from a position perpendicularly removed therefrom while the longitudinal dimension thereof projects vertically upward and perpendicular to an underlying horizontal surface; said primary body element also having a second connection means at the lower aspect thereof and a third connection means thereon;
  said sample delivery tube system comprising, at a minimum, a sample delivery tube;
  said primary body element having a centrally located longitudinally oriented hole therethrough;
  said sample delivery tube system being threaded into the centrally located longitudinally oriented hole through the primary body element so that the upper aspect of the sample delivery tube is near the upper aspect of the primary body element;
  said sample delivery tube allowing a sample solution to be entered thereto at a lower aspect thereof and be forced to flow through said sample delivery tube to the vertically upper aspect thereof;
  said third connection means on the primary body element allowing entry of a gas flow into and through the annular space formed between the outer surface of the sample delivery tube and the inner surface of the centrally located longitudinally directed hole through the primary body element;
  such that during use said sample solution flow and gas flow simultaneously eject from the upper aspects of the sample delivery tube and the annular space between the outer surface of the sample delivery tube and the inner surface of the centrally located longitudinally directed hole through the primary body element respectively and interact with one another such that the sample solution is caused to be nebulized.

25. A direct injection micro nebulizer system as in claim 24, which further comprises a top element, said top element having a centrally located longitudinally oriented hole therethrough and said top element being attached to the first connection means of the primary body element by way of complimentary connection means thereon, and said sample delivery tube being threaded through the centrally located longitudinally oriented hole in said top element so that the upper aspect thereof is positioned at near the upper aspect of the top element, and said gas flow which passes through the annular space between the outer surface of the sample delivery tube and the inner surface of the centrally located longitudinally oriented hole through the primary body element ejects from the annular space between the outer surface of the sample delivery tube and the inner surface of the centrally located longitudinally oriented hole through the top element.

26. A direct injection micro nebulizer system as in claim 25 which further comprises a tubular shaped top element tip component at the upper aspect of the top element which provides a tight tolerance inner diameter, and is made from a material which provides sstrength, is transparent to ultraviolet radiation, is not susceptable to heating and is resistant to sample deposition and accumulation thereon during use.

27. A direct injection micro nebulizer system as in claim 25 in which the top element further comprises a circumscribing tube which forms an annular space around said top element, said annular space being accessable by way of a modified top element port, through which annular space gas can be caused to flow during use to aid sample flow out of the sample delivery tube system.

28. A direct injection micro nebulizer system as in claim 24, in which the primary body element is made from hydrofloric acid resistant nonmetallic material.

29. A direct injection micro nebulizer system as in claim 24, which further comprises a chromatography column which is attached to the sample delivery tube system, through which chromatography column a sample solution flows prior to flowing through the sample delivery tube inside the primary body element.

30. A direct injection micro nebulizer system as in claim 24, in which the sample delivery tube system includes, along at least a portion of its length, a temperature control element for use in controlling the temperature thereof.

31. A direct injection micro nebulizer system as in claim 24, in which the first, second and third connection means of the primary body element comprise female screw threads.

32. A direct injection micro nebulizer system as in claim 25, in which the top element is attached to the primary body element at the first connection means thereof in a manner which allow easy removal thereof.

33. A direct injection micro nebulizer system as in claim 24, in which the first connection means of the primary body element is simply the upper aspect of the longitudinally directed centrally located hole through said primary body element.

34. A direct injection micro nebulizer system as in claim 24 which further comprises a sample delivery tube system adjustment means comprising a double nut system, with the first nut thereof having connection means complimentary to the second connection means of the primary body element, and the second nut thereof having connection means thereon which are complimentary to additional connection means in the first nut thereof and means for firmly securing the sample delivery tube system such that when the two nuts are connected to one another, and the combination is connected to the primary body element at the second connection means thereof, adjustment of the first nut connection in the second connection means of the primary body element causes the upper aspect of the sample delivery tube to be vertically adjusted.

35. A direct injection micro nebulizer system as in claim 24 which further comprises a sample delivery tube system adjustment means comprising an element which is firmly secured to the primary body element and which firmly grips the sample delivery tube system, and which is adjustable only at manufacture or at initial user utilization.

36. A direct injection micro nebulizer system as in claim 24 which further comprises a sample analysis system.

37. A direct injection micro nebulizer system as in claim 36 in which the sample analysis system Comprises a standard torch of the type used in inductively coupled plasma analysis of samples, said standard torch comprising:
   a sample injector tube which has a space therethrough, into which space the direct injection micro nebulizer system is removably inserted during use;
   an intermediate tube which concentrically surrounds the sample injector tube; and
   an outer tube which concentrically surrounds the intermediate tube.

38. A direct injection micro nebulizer system as in claim 36 in which the sample analysis system comprises a specially designed torch of the type used in the inductively coupled plasma analysis of samples, which specially designed torch comprises:
   an intermediate tube, into which intermediate tube the direct injection micro nebulizer is removably inserted during use, and
   an outer tube.

39. A direct injection micro nebulizer system as in claim 27 which further comprises a sample analysis system, said sample analysis system comprising a specially designed torch of the type used in the inductively coupled plasma analysis of samples, which specially designed torch comprises:
   means to access the modified top element port and cause a flow of gas to enter thereto during use.

40. A direct injection micro nebulizer as in claim 36, in which the sample analysis system comprises a mass spectrometer.

41. A direct injection micronebulizer system top element for use with a direct injection micro nebulizer system, said direct injection micro nebulizer top element having a centrally located longitudinally oriented hole therethrough and said direct injection micro nebulizer system top element attaching, during use, to a first connection means of a primary body element of a direct injection micro nebulizer system, through which centrally located longitudinally oriented hole through said direct injection micro nebulizer top element a sample delivery tube is, during use, threaded so that the upper aspect thereof is positioned near the upper aspect of the direct injection micro nebulizer system top element, such that during use a gas flow can be entered and caused to flow in the annular space between the outer surface of the sample delivery tube and the inner surface of the centrally located longitudinally oriented hole through the direct injection micro nebulizer top element and eject from said annular space simultaneous with sample flow through said sample delivery tube.

42. A direct injection micro nebulizer system top element as in claim 41 which further comprises an essentially tubular top element tip component at the upper aspect thereof, which top element tip component provides a tight tollerance inner diameter, provides strength, and is made from a material which is transparent to ultraviolet radiation, is not susceptable to heating and is resistant to sample deposition and accumulation thereon during use.

43. A direct injection micronebulizer system top element as in claim 41 which further comprises a circumscribing tube which forms an annular space around said direct injection micro nebulizer system top element, said annular space being accessable by way of a modified top element port, through which identified annular space gas can be caused to flow during use to aid sample flow out of the sample delivery tube system.

44. A direct injection micro nebulizer system torch of the type used in inductively couple plasma analysis of samples, into which torch a direct injection micro nebulizer system or similar geometrically sized equivalent is placed during use, said torch comprising an inner tube and an outer tube and which direct injection micro nebulizer or similar geometrically sized equivalent system inserts into said inner tube.

45. A direct injection micronebulizer system torch as in claim 44 which further comprises means for accessing a modified top element port of a direct injection micro nebulizer system top element for use with a direct injection micro nebulizer system, said direct injection micro nebulizer system top element having a centrally located longitudinally oriented hole therethrough and said direct injection micro nebulizer system top element attaching, during use, to a first connection means of a primary body element of a direct injection micro nebulizer system, through said centrally located longitudinally oriented hole a sample delivery tube is, during use, threaded so that the upper aspect thereof is positioned near the upper aspect of the direct injection micro nebulizer system top element, such that during use a gas flow can be entered and caused to flow in the annular space between the outer surface of the sample delivery tube and the inner surface of the centrally located longitudinally oriented hole through the direct injection micro nebulizer system top element and eject from said annular space simultaneous with sample flow through said sample delivery tube; said direct injection micro nebulizer system top element further comprising a circumscribing tube which forms an annular space around said direct injection micro nebulizer system top element, said annular space being accessible by way of a modified top element port, through which identified annular space gas can be caused to flow during use to aid sample flow out of the sample delivery tube system.

* * * * *